(12) United States Patent
Klein et al.

(10) Patent No.: US 8,703,435 B2
(45) Date of Patent: Apr. 22, 2014

(54) PEPTIDE BIOMARKERS OF CARDIOVASCULAR DISEASE

(75) Inventors: Jon Klein, Louisville, KY (US); Michael L. Merchant, Louisville, KY (US); Rosemary Ouseph, Louisville, KY (US); Richard A. Ward, Louisville, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 676 days.

(21) Appl. No.: 12/596,814

(22) PCT Filed: Apr. 18, 2008

(86) PCT No.: PCT/US2008/060879
§ 371 (c)(1),
(2), (4) Date: Jan. 12, 2010

(87) PCT Pub. No.: WO2008/131261
PCT Pub. Date: Oct. 30, 2008

(65) Prior Publication Data
US 2010/0124552 A1    May 20, 2010

Related U.S. Application Data

(60) Provisional application No. 60/913,069, filed on Apr. 20, 2007, provisional application No. 60/970,121, filed on Sep. 5, 2007, provisional application No. 60/970,369, filed on Sep. 6, 2007.

(51) Int. Cl.
*G01N 31/00*    (2006.01)
*G01N 33/53*    (2006.01)

(52) U.S. Cl.
USPC ........... 435/7.21; 435/7.1; 436/501; 436/518; 424/9.1; 424/520; 422/430; 530/300; 530/350

(58) Field of Classification Search
CPC ..... A61K 38/00; A61K 39/00; G01N 33/582; G01N 33/54366; G01N 33/6893; C07K 5/00; C07K 14/705; C07K 16/18
See application file for complete search history.

(56) References Cited

U.S. PATENT DOCUMENTS

| 6,890,763 | B2 | 5/2005 | Jackowski et al. |
| 2002/0081599 | A1 | 6/2002 | Curtis |
| 2005/0244905 | A1 | 11/2005 | Ischiropoulos |
| 2006/0057642 | A1 | 3/2006 | Kiefer et al. |

FOREIGN PATENT DOCUMENTS

| WO | 2005001480 | 1/2005 | |
| WO | WO 2005/001480 A1 * | 1/2005 | ............. G01N 33/68 |

OTHER PUBLICATIONS

Anderson (J Physiol., vol. 563, No. 1, 2005, pp. 23-60).*
Ottani and Galvani (Clinica Chimica Acta, vol. 311, No. 1, 2001, pp. 33-39).*
Anderson, L., "Candidate-based proteomics in the search for biomarkers of cardiovascular disease," J Physiol., 563.1, 2005, pp. 23-60.
Charytan et al., "The use of invasive cardiac procedures after acute myocardial infarction in long-term dialysis subjects," Am Heart J., 152, 2006, pp. 558-564.
Chertov et al., "Organic solvent extraction of proteins and peptides from serum as an effective sample preparation for detection and identification of biomarkers by mass spectrometry," Proteomics, 4, 2004, pp. 1195-1203.
Cushman et al., "C-reactive protein and the 10-year incidence of coronary heart disease in older men and women: the cardiovascular health study," Circulation, 112, 2005, pp. 25-31.
Danesh et al., "Plasma fibrinogen level and the risk of major cardiovascular diseases and nonvascular mortality: an individual participant meta-analysis," JAMA, 294, 2005, pp. 1799-1809.
Danesh et al., "Association of fibrinogen, C-reactive protein, albumin, or leukocyte count with coronary heart disease: meta-analyses of prospective studies," JAMA, 279, 1998, pp. 1477-1482.
Danesh et al., "Fibrin D-dimer and coronary heart disease: prospective study and meta-analysis," Circulation, 103, 2001, pp. 2323-2327.
Decramer et al., "Predicting the clinical outcome of congenital unilateral ureteropelvic junction obstruction in newborn by urinary proteome analysis," Nat Med, 12, 2006, pp. 398-400.
Donahue et al., "Discovery of proteins related to coronary artery disease using industrial-scale proteomics analysis of pooled plasma," Am Heart J, 152, 2006, pp. 478-485.
Go et al., "Chronic kidney disease and the risks of death, cardiovascular events, and hospitalization," N Engl J Med, 351, 2004, pp. 1296-1305.
Hase et al., "Risk factors for de novo acute cardiac events in subjects initiating hemodialysis with no previous cardiac symptom," Kidney Int, 70, 2006, pp. 1142-1148.
Hase et al., Independent risk factors for progression of coronary atherosclerosis in hemodialysis subjects, Ther Apher Dial, 10, 2006, pp. 321-327.
Herzog et al., Poor long-term survival after acute myocardial infarction among subjects on long-term dialysis, N Engl J Med, 339, 1998, pp. 799-805.
Kaysen et al., "Evidence that C-reactive protein or IL-6 are not surrogates for all inflammatory cardiovascular risk factors in hemodialysis subjects," Blood Purif, 24, 2006, pp. 508-516.

(Continued)

*Primary Examiner* — Lisa Cook
(74) *Attorney, Agent, or Firm* — Stites & Harbison PLLC; Terry L. Wright

(57) ABSTRACT

The presently-disclosed subject matter provides methods for diagnosing a cardiovascular disease in a subject by determining an amount of one or more peptide biomarkers disclosed herein in a biological sample from the subject. The presently-disclosed subject matter further provides methods for determining treatment efficacy and/or progression of a cardiovascular disease in a subject by measuring amounts of one or more of the biomarkers in a biological sample from the subject. The presently-disclosed subject matter also provides antibodies and kits for measuring the biomarkers.

28 Claims, 6 Drawing Sheets

(56) References Cited

OTHER PUBLICATIONS

Kuzdzal et al., "Biomarker discovery and analysis platform: application to Alzheimer's disease," Biotechniques, 39, 2005, pp. 606-607.

Liu et al., "Association between cholesterol level and mortality in dialysis subjects: role of inflammation and malnutrition," JAMA, 291, 2004, pp. 451-459.

Lopez et al., "A novel, high-throughput workflow for discovery and identification of serum carrier protein-bound peptide biomarker candidates in ovarian cancer samples," Clin Chem, 53, 2007, pp. 1067-1074.

Lowenthal et al., "Analysis of albumin-associated peptides and proteins from ovarian cancer subjects," Clin Chem, 51, 2005, pp. 1933-1945.

Mangoni et al., "Homocysteine and cardiovascular disease: current evidence and future prospects," Am J Med, 112, 2002, pp. 556-565.

Martin-Ventura et al., "Proteomics in atherothrombosis: a future perspective," Expert Rev Proteomics, 4, 2007, pp. 249-260.

Ohtake et al., "High prevalence of occult coronary artery stenosis in subjects with chronic kidney disease at the initiation of renal replacement therapy: an angiographic examination," J Am Soc Nephrol, 16, 2005, pp. 1141-1148.

Parekh et al., "Incidence of atherosclerosis by race in the dialysis morbidity and mortality study: a sample of the US ESRD population," J Am Soc Nephrol, 16, 2005, pp. 1420-1426.

Petricoin et al., "The blood peptidome: a higher dimension of information content for cancer biomarker discovery," Nat Rev Cancer, 6, 2006, pp. 961-967.

Rane et al., "Heat shock protein 27 controls apoptosis by regulating Akt activation," J Biol. Chem, 278, 2003, pp. 27828-27835.

Rane et al., "Gamma-amino butyric acid type B receptors stimulate neutrophil chemotaxis during ischemia-reperfusion," J Immunol, 174, 2005, pp. 7242-7249.

Scott et al., "Mammalian BMP-1/Tolloid-related metalloproteinases, including novel family member mammalian Tolloid-like 2, have differential enzymatic activities and distributions of expression relevant to patterning and skeletogenesis," Dev Biol, 213, 1999, pp. 283-300.

Sonel et al., Prospective Study Correlating Fibrinopeptide A, Troponin I, Myoglobin, and Myosin Light Chain Levels With Early and Late Ischemic Events in Consecutive Patients Presenting to the Emergency Department With Chest Pain, Circulation, 102, 2000, pp. 1107-1113.

Trespalacios et al., "Incident acute coronary syndromes in chronic dialysis subjects in the United States," Kidney Int, 62, 2002, pp. 1799-1805.

Villanueva et al., "Serum peptidome patterns that distinguish metastatic thyroid carcinoma from cancer-free controls are unbiased by gender and age," Mol Cell Proteomics, 5, 2006, pp. 1840-1852.

Villanueva et al., Correcting common errors in identifying cancer-specific serum peptide signatures, J Proteome Res, 4, 2005, pp. 1060-1072.

Wang et al., "Multiple biomarkers for the prediction of first major cardiovascular events and death," N Engl J Med, 355, 2006, pp. 2631-2639.

Weiner et al., "The Framingham predictive instrument in chronic kidney disease," J Am Coll Cardiol, 50, 2007, pp. 217-224.

Zager et al., "U" curve association of blood pressure and mortality in hemodialysis subjects. Kidney Int, 54:2, 1998, pp. 561-569.

Zhang et al., "Inhibition of bone morphogenetic protein 1 by native and altered forms of alpha2-macroglobulin," J Biol Chem, 281, 2006, pp. 39096-39104.

Zimmerli et al., "Urinary proteomic biomarkers in coronary artery disease," Mol Cell Proteomics, 7, 2008, pp. 290-298.

ISA/US, International Search Report and Written Opinion for international application No. PCT/US08/60879, mailed Nov. 18, 2008.

* cited by examiner 1616.663 m/z 1991.892 m/z

PEPTIDE BIOMARKERS OF CARDIOVASCULAR DISEASE

RELATED APPLICATIONS

The presently disclosed subject matter claims the benefit of U.S. Provisional Patent Application Ser. No. 60/913,069, filed Apr. 20, 2007; U.S. Provisional Patent Application Ser. No. 60/970,121, filed Sep. 5, 2007; and U.S. Provisional Patent Application Ser. No. 60/970,369, filed Sep. 6, 2007; the disclosures of each of which is incorporated herein by reference in their entireties.

TECHNICAL FIELD

The presently disclosed subject matter relates to methods for diagnosing cardiovascular disease in a subject. In particular, the presently disclosed subject matter relates to methods for diagnosing cardiovascular disease in a subject by determining amounts of one or more peptide biomarkers in a biological sample from the subject.

BACKGROUND

Cardiovascular diseases (CVDs) are debilitating illnesses that afflict millions of people in the world each year. Indeed, in 1997, over 450,000 people in the U.S. alone died from myocardial infarctions; one of every five deaths in that calendar year. In addition to myocardial infarction, cardiovascular diseases result in hypertension, angina, arteriosclerosis, and atherosclerosis. Angina, for example, accounts for more than 1 million hospital admissions annually in the U.S., and 6-8 percent of subjects with this condition either have nonfatal myocardial infarction, or die, within the first year after diagnosis.

Cardiovascular diseases are also a major cause of morbidity and mortality in subsets of the population already suffering from other disorders. For example, cardiovascular disease are the major cause of mortality in end-stage renal disease (ESRD) subjects (1). Coronary artery disease (CAD) is reported to occur in 40-60% of incident hemodialysis subjects and this figure rises to more than 50% for diabetic hemodialysis subjects (1-3). The annual incidence of new coronary artery disease in dialysis subjects is 30-40 times higher than in the general population (4). The rate at which hemodialysis subjects in the United States are hospitalized for their first acute coronary event (myocardial infarction or unstable angina) is 2.9-3.3 per 100 subject-years (5) and the annual overall mortality and cardiac mortality following acute myocardial infarction were 62% and 42%, respectively, between 1990 and 1995 (6). Moreover, hemodialysis subjects are significantly less likely to be evaluated with cardiac catheterization and therefore have a lower incidence of coronary revascularization procedures (7).

Hence, the ability to accurately identify subjects with CVDs in the general population, as well as in subpopulations identified as at high risk for CVDs, such as the ESRD population, is of great importance.

Currently, physicians are able to diagnose CVD in subjects who have already begun to experience symptoms. For example, the levels of certain cardiac-associated enzymes, such as creatine kinase, are elevated after myocardial infarction, and may be detected an enzyme-specific assay. Likewise, coronary angiography is the definitive means of diagnosing CAD. However, it is an expensive and invasive procedure. Algorithms have been developed for non-invasively assessing the risk of CAD in the general population. These algorithms are based on well-established risk factors, including dyslipidemia, smoking, hypertension and diabetes. While studies show that at least one of these risk factors is present in 80-90% of subjects with coronary artery disease in the general population, it has been estimated that they explain only about 75% of the occurrence of CAD. Further, traditional risk factors for CAD derived from studies of the normal population have limited applicability in at risk subpopulations, such as for example hemodialysis subjects. The prevalence of dyslipidemia, hypertension, diabetes and left ventricular hypertrophy is higher in hemodialysis subjects than in the general population and the relationship between some of these traditional risk factors and cardiovascular outcomes appears to be different in hemodialysis subjects than it is in the normal population. For example, the relationship of both hypertension and cholesterol to coronary heart disease and mortality is U-shaped in hemodialysis subjects, with higher blood pressures and cholesterol concentrations conferring a survival advantage (8, 9).

CVD constitutes a considerable medical and economic burden. Current diagnostic approaches are either invasive, expensive, associated with the risk of complications, or their interpretation is confounded by concurrent medical conditions. Alternative, non-invasive approaches are needed that address these limitations. Thus, there is currently an unmet need for new, more specific biomarkers of CVD that can be used to identify subjects suffering from (even if physiologically asymptomatic) or at risk of CVD for targeted interventions.

SUMMARY

This Summary lists several embodiments of the presently disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this Summary or not. To avoid excessive repetition, this Summary does not list or suggest all possible combinations of such features.

In some embodiments of the presently-disclosed subject matter, a method for diagnosing a cardiovascular disease in a subject is provided. In some embodiments, the method comprises determining an amount of at least one peptide of Table 2, Table 3, or both in a biological sample from the subject and comparing the amount of the at least one peptide in the sample with a control level, wherein if the amount determined in the sample is different than the control level, the subject is diagnosed as having, or at an increased risk of developing, the cardiovascular disease.

In some embodiments of the presently-disclosed subject matter, a method for determining treatment efficacy and/or progression of a cardiovascular disease in a subject is provided. In some embodiments, the method comprises determining an amount of at least one peptide of Table 2, Table 3, or both in a first biological sample collected from the subject at a first time point; determining an amount of the at least one peptide of Table 1 in a second biological sample from the subject at a second time point; and comparing the amounts of the at least one peptide in the first and second samples, wherein a change in the amounts of the at least one peptide from the first and second samples is correlated with determining treatment efficacy and/or progression of the cardiovascular disease in the subject. In some embodiments, the first time point is prior to initiation of a treatment for the cardiovascular disease and the second time point is after initiation of the treatment. In other embodiments, the first time point is prior to onset of the cardiovascular disease and the second time point is after onset of the cardiovascular disease.

In some embodiments of the methods, the at least one peptide comprises one or more peptides selected from the group consisting of protocadherin-20 (PCDH-20), tolloid-like 2 protein (TLL-2), mammalian tolloid protein (mTLD), bone morphogenetic protein-1 (BMP-1), phosphorylated fibrinopeptide A, chondroitin beta-1,4-N-acetylgalactosaminyltransferase 2 (CSGalNAcT-2), and fragments thereof. In some embodiments, the at least one peptide is a plurality of peptides.

In some embodiments of the methods, determining the amount of the at least one peptide comprises determining the amount of the at least one peptide in the sample using mass spectrometry (MS) analysis (e.g., matrix-assisted laser desorption/ionization (MALDI) time-of-flight (TOF) MS analysis or electrospray ionization (ESI) MS), immunoassay analysis (e.g., enzyme-linked immunosorbent assay (ELISA)), or both.

In some embodiments of the methods, the at least one peptide is isolated from a fraction of the sample selected from the group consisting of a bound fraction and an unbound fraction. In some embodiments, the bound fraction is a an albumin-bound fraction or an immunoglobulin-bound fraction.

In some embodiments, the samples are independently selected from a saliva sample, a blood sample, a serum sample, a plasma sample, or a urine sample.

In some embodiments of the methods, the subject is human. In some embodiments the subject is a diabetic subject.

In some embodiments of the methods, the cardiovascular disease is a coronary artery disease (CAD) (e.g., atherosclerosis), a peripheral vascular disease, or both.

The presently-disclosed subject matter further provides methods for treating a cardiovascular disease in a subject. In some embodiments, the methods comprise administering to the subject an effective amount of a fibrinopeptide A polypeptide inhibitor molecule.

The presently-disclosed subject matter further provides antibodies or fragments thereof that specifically recognize a peptide of Table 2, Table 3, or both; a peptide associated with a peptide of Table 2, Table 3, or both; or combinations thereof.

The presently-disclosed subject matter further provides kits for detecting cardiovascular disease, or a risk thereof, in a subject. In some embodiments, the kit comprises one or more antibodies that specifically recognize a peptide of Table 2, Table 3, or both; a peptide associated with a peptide of Table 2, Table 3, or both; or combinations thereof. In some embodiments, the one or more antibodies are a plurality of different antibodies. In some embodiments, the antibodies are bound to a substrate. In some embodiments, the kit comprises instructions for using the kit.

Accordingly, it is an object of the presently disclosed subject matter to measure peptide biomarkers of cardiovascular disease in a subject. This object is achieved in whole or in part by the presently disclosed subject matter.

An object of the presently disclosed subject matter having been stated hereinabove, and which is achieved in whole or in part by the presently disclosed subject matter, other objects and advantages will become evident to those of ordinary skill in the art after a study of the following description of the presently disclosed subject matter, figures, and non-limiting examples.

BRIEF DESCRIPTION OF THE DRAWINGS

FIG. 5A is a representative immunoblot of the highly abundant serum protein fraction for mTLD expression. FIG. 5B is a graph showing quantitative densitometry of the immunoblot data. A statistically significant (*p<0.001) increased amount of mTLD was bound to highly abundant proteins in serum of subjects with CAD as compared to serum of subjects without CAD.

FIG. 6A is a representative immunoblot of the highly abundant serum protein fraction for BMP-1 expression. Lanes 1-4 of FIG. 6A are serum from four different subjects with CAD; Lanes 5-8 of FIG. 6A are samples from four different subjects without CAD; Lane 9 of FIG. 6A is pooled normal male serum, Lane 10 of FIG. 6A is synthetic BMP-1 positive control, and Lane 11 of FIG. 6A is BioRad PRECISION PLUS™ prestained molecular weight standards. FIG. 6B is a graph showing quantitative densitometry of immunoblot data. A statistically significant (#p<0.0001) increased amount of mature BMP-1 was bound to highly abundant serum proteins in serum of subjects without CAD as compared to serum of subjects with CAD.

BRIEF DESCRIPTION OF THE TABLES

Figure 1:
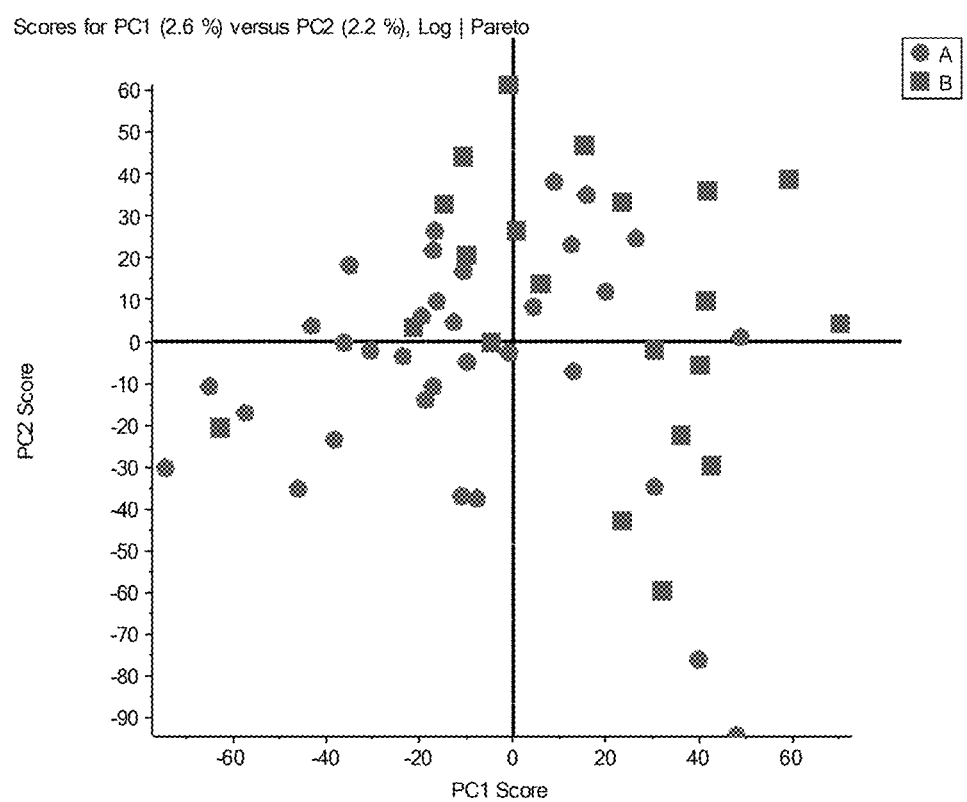
FIG. 1 is a graph showing multivariate analysis of peptide expression using principal components analysis (PCA). PCA scoring plot for comparison of MALDI-TOF MS data developed from direct MS analysis of free, unbound serum peptides extracted from serum of subjects with CAD (circles) and subjects without CAD (squares). Unsupervised sorting of samples into groups indicates the variation in the data is a result of differentially expressed serum peptides.

Table 1 shows demographic and biochemical characteristics of subjects with and without CAD. Data are presented as mean±SD. No significant differences in these parameters were noted between two groups.

Table 2 shows serum peptides differentially expressed between subjects with and without CAD. MALDI-TOF MS spectra were obtained, aligned, and compared as described under the Methods section of the Examples. Differential expression was determined using Student's t-test after manual review of the primary MALDI-TOF MS data. There were no differences in the expression of peptides bound to albumin/IgG or released during albumin/IgG depletion.

Table 3 shows assignment of peptide sequences to differentially expressed serum peptides. Peptides with significant differential expression (Table 2) were selected for tandem MS analyses. Primary MALDI-TOF MS spectra were reviewed to determine if the observed masses were noise or if other peptide masses were occupying ±1.0 m/z TOF space (which would interfere with tandem MS data acquisition).

BRIEF DESCRIPTION OF THE SEQUENCE LISTING

SEQ ID NO: 1 and SEQ ID NO: 7 are amino acid sequences of a portion of a human fibrinogen alpha chain peptide.

SEQ ID NO: 2 and SEQ ID NO: 8 are amino acid sequences of another portion of a human fibrinogen alpha chain peptide.

SEQ ID NO: 3 and SEQ ID NO: 9 are amino acid sequences of a portion of a tolloid-like 2 peptide.

SEQ ID NO: 4 and SEQ ID NO: 10 are amino acid sequences of a portion of a bone morphogenetic protein-1 peptide.

SEQ ID NO: 5 and SEQ ID NO: 11 are amino acid sequences of a portion of a protocadherin-20 peptide.

SEQ ID NO: 6 and SEQ ID NO: 12 are amino acid sequences of a portion of a chondroitin beta-1,4-N-acetylgalactosaminyltransferase 2 peptide.

DETAILED DESCRIPTION

The details of one or more embodiments of the presently disclosed subject matter are set forth in the accompanying description below. Other features, objects, and advantages of the presently disclosed subject matter will be apparent from the detailed description, figures, and claims. All publications, patent applications, patents, and other references mentioned herein are incorporated by reference in their entirety. Some of the polynucleotide and polypeptide sequences disclosed herein are cross-referenced to GenBank, Swiss-Prot, or other public database accession numbers. The sequences cross-referenced in the GenBank, Swiss-Prot, or other public database are expressly incorporated by reference as are equivalent and related sequences present in GenBank, Swiss-Prot, or other public databases. Also expressly incorporated herein by reference are all annotations present in the GenBank, Swiss-Prot, or other public databases associated with the sequences disclosed herein. In case of conflict, the present specification, including definitions, will control.

Unless defined otherwise, all technical and scientific terms used herein have the same meaning as commonly understood to one of ordinary skill in the art to which the presently disclosed subject matter belongs. Although any methods, devices, and materials similar or equivalent to those described herein can be used in the practice or testing of the presently disclosed subject matter, representative methods, devices, and materials are now described.

Following long-standing patent law convention, the terms "a", "an", and "the" refer to "one or more" when used in this application, including the claims. Thus, for example, reference to "a cell" or "a virus" includes a plurality of such cells or viruses, respectively, and so forth.

Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in this specification and attached exemplary claims are approximations that can vary depending upon the desired properties sought to be obtained by the presently disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

Cardiovascular diseases (CVDs) are a leading cause of disability and death in the developed world, resulting in more premature deaths than any other illness. Unsurprisingly, treatment of CVD represents a very high cost burden to any healthcare system. Accordingly, there is tremendous social and political pressure to develop earlier and more reliable diagnostic tests to assist in the detection, treatment, and prevention of CVD. The presently disclosed subject matter provides methods and compositions for diagnosing CVD, or the risk thereof, in subjects, as well as monitoring CVD treatment efficacy and disease progression in the subjects.

Cardiovascular disease refers to the class of diseases that involve the heart and/or blood vessels (arteries and veins). CVD, as the term is used herein, can refer to any disease that affects the cardiovascular system, such as for example coronary artery disease (CAD) and peripheral vascular disease (PVD). These and other CVD conditions have related causes, mechanisms, and treatments. In practice, CVD can be treated by cardiologists, thoracic surgeons, vascular surgeons, neurologists, and interventional radiologists, depending on the organ system that is being treated. There is considerable overlap in the specialties, and it is common for certain procedures to be performed by different types of specialists in the same hospital.

"Peripheral vascular disease" (PVD) as used herein, also known as peripheral artery occlusive disease (PAOD) or peripheral artery disease (PAD), is a collator for multiple diseases caused by the obstruction of large peripheral arteries, which can result from atherosclerosis, inflammatory processes leading to stenosis, an embolism or thrombus formation. It can cause either acute or chronic ischemia.

"Coronary artery disease" (CAD) as used herein, also called coronary heart disease (CHD), ischemic heart disease, and atherosclerotic heart disease, is the end result of the accumulation of atheromatous plaques within the walls of the arteries that supply the myocardium (the muscle of the heart). While the symptoms and signs of CAD are noted in the advanced state of disease, most individuals with CAD show no symptoms of disease for decades even as the disease progresses. Unfortunately, the first onset of symptoms may be a "sudden" life-threatening heart attack. After decades of progression, some of these atheromatous plaques may rupture and (along with the activation of the blood clotting system) start limiting blood flow to the heart muscle. The disease is a common cause of sudden death and is also a very common reason for death of men and women over 65 years of age.

Thus, a subject may be afflicted with a CVD, such as for example CAD or PVD, for an extended time without an overt manifestation of symptoms. As such, the presently disclosed subject matter provides methods and peptide biomarkers that can be utilized to diagnose or predict the risk of developing a CVD in a subject in advance of clinical manifestations of the disease, thereby providing earlier treatment opportunities.

In some embodiments of the presently disclosed subject matter, a method for diagnosing a cardiovascular disease in a subject is provided. In some embodiments, the method comprises obtaining a biological sample from the subject and determining an amount (including a qualitative determination of the presence or absence) of at least one peptide biomarker associated with CVD, such as for example one or more peptides set forth in Tables 2 and 3. In some embodiments, the peptide biomarkers comprise one or more peptides selected from the group consisting of protocadherin-20 (PCDH-20), tolloid-like 2 protein (TLL-2), mammalian tolloid protein (mTLD), bone morphogenetic protein-1 (BMP-1), fibrinopeptide A (FPA, also known as fibrinogen α-chain), phosphorylated fibrinopeptide A (pFPA), chondroitin beta-1,4-N-acetylgalactosaminyltransferase 2 (CSGalNAcT-2), and fragments thereof. The method can further comprise comparing the amount of the at least one peptide in the sample with a control level. If the amount determined from the sample differs from (e.g., is greater than or is less than) the control level, the subject can be diagnosed as having, or being at an increased risk of developing, the cardiovascular disease.

As one example, in some embodiments, a subject can be diagnosed as having, or at risk of developing, a CVD if biomarker levels in a biological sample from the subject for one or more of PCDH-20, TLL-2, mTLD, FPA, pFPA, and/or fragments thereof are increased as compared to control levels. Alternatively, or in conjunction with increases in these biomarker levels, the subject can be diagnosed as having, or at risk of developing, a CVD if biomarker levels in a biological sample from the subject for one or more of BMP-1, CSGalNAcT-2, and/or fragments thereof are decreased as compared to control levels.

In some particular embodiments, the biomarkers are measured from a particular fraction of the biological sample. More specifically, in some particular embodiments, the biomarkers are measured in a serum fraction of peptides bound to other peptides (e.g., albumin, immunoglobulins, or other abundant proteins). That is, the biomarker peptides are not free in whole serum, but rather are bound to one or more other proteins present in the serum. Biological samples can be fractionated using any of several methodologies known in the art, including for example, immunodepletion strategies.

The terms "polypeptide", "protein", and "peptide", which are used interchangeably herein, refer to a polymer of the 20 protein amino acids, including modified amino acids (e.g., phosphorylated, glycated, etc.) and amino acid analogs, regardless of its size or function. Although "protein" is often used in reference to relatively large polypeptides, and "peptide" is often used in reference to small polypeptides, usage of these terms in the art overlaps and varies. The term "peptide" as used herein refers to peptides, polypeptides, proteins and fragments of proteins, unless otherwise noted. The terms "protein", "polypeptide" and "peptide" are used interchangeably herein when referring to a gene product and fragments thereof. Thus, exemplary polypeptides include gene products, naturally occurring proteins, homologs, orthologs, paralogs, fragments and other equivalents, variants, fragments, and analogs of the foregoing.

The terms "polypeptide fragment" or "fragment", when used in reference to a polypeptide, refers to a polypeptide in which amino acid residues are absent as compared to the full-length polypeptide itself, but where the remaining amino acid sequence is usually identical to the corresponding positions in the reference polypeptide. Such deletions can occur at the amino-terminus or carboxy-terminus of the reference polypeptide, or alternatively both. Fragments typically are at least 5, 6, 8 or 10 amino acids long, at least 14 amino acids long, at least 20, 30, 40 or 50 amino acids long, at least 75 amino acids long, or at least 100, 150, 200, 300, 500 or more amino acids long.

A fragment can retain one or more of the biological activities of the reference polypeptide. In some embodiments, a fragment can comprise a domain or feature, and optionally additional amino acids on one or both sides of the domain or feature, which additional amino acids can number from 5, 10, 15, 20, 30, 40, 50, or up to 100 or more residues. Further, fragments can include a sub-fragment of a specific region, which sub-fragment retains a function of the region from which it is derived. When the term "peptide" is used herein, it is intended to include the full-length peptide as well as fragments of the peptide. Thus, an identified fragment of a peptide (e.g., see Tables 2 and 3) is intended to encompass the fragment as well as the full-length peptide. For example, when reference is made herein to antibodies specific for the peptides of Tables 2 and/or 3, it is intended that the antibodies can have specificity for the peptide fragment and/or the full-length peptide from which it is derived.

The term "biological sample" as used herein refers to any body fluid or tissue potentially comprising one or more biomarkers associated with CVD. In some embodiments, for example, the biological sample can be a saliva sample, a blood sample, a serum sample, a plasma sample, a urine sample, or sub-fractions thereof.

The terms "diagnosing" and "diagnosis" as used herein refer to methods by which the skilled artisan can estimate and even determine whether or not a subject is suffering, or at risk of suffering from, a given disease or condition. The skilled artisan often makes a diagnosis on the basis of one or more diagnostic indicators, such as for example a biomarker, the amount (including presence or absence) of which is indicative of the development risk, presence, severity, or absence of the condition. Thus, "diagnosing" and "diagnosis" as used herein refers to determining presence and/or severity of a condition as well as predicting a risk for developing the condition.

Along with diagnosis, clinical prognosis is also an area of great concern and interest. It is important to know the rate of progression and severity of a disease in order to plan the most effective therapy. If a more accurate prognosis can be made, appropriate therapy, and in some instances less severe therapy for the patient can be chosen. Measurement of CVD biomarkers can be useful in order to separate subjects with good prognosis who will need no further therapy from those more likely to develop severe disease and who might benefit from more intensive treatments.

As such, "making a diagnosis" or "diagnosing", as used herein, is further inclusive of making a prognosis, which can provide for predicting a clinical outcome (with or without medical treatment), selecting an appropriate treatment (or whether treatment would be effective), or monitoring a current treatment and potentially changing the treatment, based on the measure of the peptide biomarkers disclosed herein.

In some embodiments of the presently disclosed subject matter, multiple determination of one or more diagnostic or prognostic peptide biomarkers can be made, and a temporal change in the biomarker can be used to monitor the risk for development, development, or progression of disease and/or efficacy of appropriate therapies directed against the disease. In such an embodiment for example, one might expect to see a decrease or an increase in the peptide biomarker(s) over time prior to initiation of and/or during the course of effective therapy. Thus, the presently disclosed subject matter provides in some embodiments a method for determining treatment efficacy and/or progression of a cardiovascular disease in a subject. In some embodiments, the method comprises determining an amount of at least one peptide biomarker associated with a CVD, such as for example at least one peptide of Tables 2 and 3, in biological samples collected from the subject at a plurality of different time points and comparing the amounts of the at least one peptide in the samples collected at different time points. For example, a first time point can be selected prior to initiation of a treatment and a second time point can be selected at some time after initiation of the treatment. One or more biomarker levels can be measured in each of the samples taken from different time points and qualitative and/or quantitative differences noted. A change in the amounts of the biomarker levels from the first and second samples can be correlated with determining treatment efficacy and/or progression of the disease in the subject.

The terms "correlated" and "correlating," as used herein in reference to the use of diagnostic and prognostic biomarkers, refers to comparing the presence or quantity of the biomarker in a subject to its presence or quantity in subjects known to suffer from, or known to be at risk of, a given condition (e.g., a CVD); or in subjects known to be free of a given condition, i.e. "normal individuals". For example, a biomarker level in a biological sample can be compared to a level known to be associated with a specific type of CVD. The sample's biomarker level is said to have been correlated with a diagnosis; that is, the skilled artisan can use the biomarker level to determine whether the subject suffers from a specific type of CVD, and respond accordingly. Alternatively, the sample's biomarker level can be compared to a control marker level known to be associated with a good outcome (e.g., the absence of CVD), such as an average level found in a population of normal subjects.

In certain embodiments, a diagnostic or prognostic biomarker is correlated to a condition or disease by merely its presence or absence. In other embodiments, a threshold level of a diagnostic or prognostic biomarker can be established, and the level of the indicator in a subject sample can simply be compared to the threshold level. In some embodiments, a threshold level for the presently disclosed biomarkers associated with CVD is about 25 pg/mL, about 50 pg/mL, about 60 pg/mL, about 75 pg/mL, about 100 pg/mL, about 150 pg/mL, about 200 pg/mL, about 300 pg/mL, about 400 pg/mL, about 500 pg/mL, about 600 pg/mL, about 750 pg/mL, about 1000 pg/mL, or about 2500 pg/mL.

As noted, in some embodiments, multiple determinations of one or more diagnostic or prognostic biomarkers can be made, and a temporal change in the marker can be used to determine a diagnosis or prognosis. For example, a diagnostic marker can be determined at an initial time, and again at a second time. In such embodiments, an increase or decrease (depending on biomarker measured) in the marker from the initial time to the second time can be diagnostic of a particular type of CVD, or a given prognosis. Likewise, a decrease in the marker from the initial time to the second time can be indicative of a particular type of CVD, or a given prognosis. Furthermore, the degree of change of one or more markers can be related to the severity of CVD and future adverse events.

The skilled artisan will understand that, while in certain embodiments comparative measurements can be made of the same diagnostic marker at multiple time points, one can also measure a given marker at one time point, and a second marker at a second time point, and a comparison of these markers can provide diagnostic information.

The phrase "determining the prognosis" as used herein refers to methods by which the skilled artisan can predict the course or outcome of a condition in a subject. The term "prognosis" does not refer to the ability to predict the course or outcome of a condition with 100% accuracy, or even that a given course or outcome is predictably more or less likely to occur based on the presence, absence or levels of test biomarkers. Instead, the skilled artisan will understand that the term "prognosis" refers to an increased probability that a certain course or outcome will occur; that is, that a course or outcome is more likely to occur in a subject exhibiting a given condition, when compared to those individuals not exhibiting the condition. For example, in individuals not exhibiting the condition (e.g., not expressing the biomarker(s) or expressing at a reduced level), the chance of a given outcome may be about 3%. In certain embodiments, a prognosis is about a 5% chance of a given outcome, about a 7% chance, about a 10% chance, about a 12% chance, about a 15% chance, about a 20% chance, about a 25% chance, about a 30% chance, about a 40% chance, about a 50% chance, about a 60% chance, about a 75% chance, about a 90% chance, or about a 95% chance.

The skilled artisan will understand that associating a prognostic indicator with a predisposition to an adverse outcome is a statistical analysis. For example, a biomarker level (e.g., quantity of expression in a sample) of greater than a control level in some embodiments can signal that a subject is more likely to suffer from a CVD than subjects with a level less than or equal to the control level, as determined by a level of statistical significance. Additionally, a change in marker concentration from baseline levels can be reflective of subject prognosis, and the degree of change in marker level can be related to the severity of adverse events. Statistical significance is often determined by comparing two or more populations, and determining a confidence interval and/or a p value. See, e.g., Dowdy and Wearden, Statistics for Research, John Wiley & Sons, New York, 1983, incorporated herein by reference in its entirety. Preferred confidence intervals of the present subject matter are 90%, 95%, 97.5%, 98%, 99%, 99.5%, 99.9% and 99.99%, while preferred p values are 0.1, 0.05, 0.025, 0.02, 0.01, 0.005, 0.001, and 0.0001.

In other embodiments, a threshold degree of change in the level of a prognostic or diagnostic biomarker can be established, and the degree of change in the level of the indicator in a biological sample can simply be compared to the threshold degree of change in the level. A preferred threshold change in the level for markers of the presently disclosed subject matter is about 5%, about 10%, about 15%, about 20%, about 25%, about 30%, about 50%, about 75%, about 100%, and about 150%. In yet other embodiments, a "nomogram" can be established, by which a level of a prognostic or diagnostic indicator can be directly related to an associated disposition towards a given outcome. The skilled artisan is acquainted with the use of such nomograms to relate two numeric values with the understanding that the uncertainty in this measurement is the same as the uncertainty in the marker concentration because individual sample measurements are referenced, not population averages.

Numerous methods and devices are well known to the skilled artisan for the detection and analysis of the biomarker peptides of the presently disclosed subject matter. With regard to polypeptides or proteins in subject test samples, mass spectrometry and/or immunoassay devices and methods can be used, although other methods are well known to those skilled in the art (for example, the measurement of marker RNA levels). See, e.g., U.S. Pat. Nos. 6,143,576; 6,113,855; 6,019,944; 5,985,579; 5,947,124; 5,939,272; 5,922,615; 5,885,527; 5,851,776; 5,824,799; 5,679,526; 5,525,524; and 5,480,792, each of which is hereby incorporated by reference in its entirety. These devices and methods can utilize labeled molecules in various sandwich, competitive, or non-competitive assay formats, to generate a signal that is related to the presence or amount of an analyte of interest. Additionally, certain methods and devices, such as biosensors and optical immunoassays, can be employed to determine the presence or amount of analytes without the need for a labeled molecule. See, e.g., U.S. Pat. Nos. 5,631,171; and 5,955,377, each of which is hereby incorporated by reference in its entirety.

In certain embodiments of the presently disclosed subject matter, the biomarker peptides are analyzed using an immunoassay. The presence or amount of a marker can be determined using antibodies or fragments thereof specific for each marker and detecting specific binding. For example, in some embodiments, the antibody specifically binds a peptide of Tables 2 and/or 3, which is inclusive of antibodies that bind a full-length protein or fragments thereof. The antibody can in some embodiments instead specifically bind a peptide associated with a peptide of Tables 2 and/or 3. For example, as shown in Table 2, some of the marker peptides are isolated from the biological fluid bound to one or more other peptides (e.g., bound to immunoglobulins, albumin, or other highly abundant proteins), and so antibodies specific for the other peptides can be useful for isolating and identifying the marker peptide(s) of interest. Further, in some embodiments, the antibody can have binding specificity for specific forms of marker peptides, such as for example phosphorylated and unphosphorylated forms of marker peptides, including but not limited to antibodies that are specific for either phosphorylated or unphosphorylated fibrinopeptide A.

Any antibody which effectively binds one or more peptide biomarkers disclosed herein is within the scope of the presently-disclosed subject matter. This includes by way of example, polyclonal and monoclonal antibodies, recombinant antibodies, chimeric antibodies, humanized antibodies, bispecific antibodies, single chain antibodies, antibodies from different species (e.g., mouse, goat, rabbit, human, rat, bovine, etc.), anti-idiotypic antibodies, antibodies of different isotype (IgG, IgM, IgE, IgA, etc.), as well as fragments and derivatives thereof (e.g., (Fab)$_2$, Fab, Fv, Fab, 2(Fab), Fab', (Fab')$_2$ fragments). In some particular embodiments, the antibody is a monoclonal antibody.

Any suitable immunoassay can be utilized, for example, enzyme-linked immunoassays (ELISA), radioimmunoassays (RIAs), competitive binding assays, and the like. Specific immunological binding of the antibody to the marker can be detected directly or indirectly. Direct labels include fluorescent or luminescent tags, metals, dyes, radionuclides, and the like, attached to the antibody. Indirect labels include various enzymes well known in the art, such as alkaline phosphatase, horseradish peroxidase and the like.

The use of immobilized antibodies or fragments thereof specific for the peptide biomarkers is also contemplated by the present subject matter. The antibodies can be immobilized onto a variety of solid supports, such as magnetic or chromatographic matrix particles, the surface of an assay plate (such as microtiter wells), pieces of a solid substrate material (such as plastic, nylon, paper), and the like. An assay strip can be prepared by coating the antibody or a plurality of antibodies in an array on solid support. This strip can then be dipped into the test biological sample and then processed quickly through washes and detection steps to generate a measurable signal, such as for example a colored spot.

In some embodiments, a kit for the analysis of biomarkers is provided that comprises antibodies having specificity for one or more biomarkers associated with CVD. Such a kit can comprise devices and reagents for the analysis of at least one test sample. The kit can further comprise instructions for using the kit and conducting the analysis. Optionally the kits can contain one or more reagents or devices for converting a marker level to a diagnosis or prognosis of the subject.

In some embodiments, mass spectrometry (MS) analysis can be used alone or in combination with other methods (e.g., immunoassays) to determine the presence and/or quantity of the one or more biomarkers of interest in a biological sample. In some embodiments, the MS analysis comprises matrix-assisted laser desorption/ionization (MALDI) time-of-flight (TOF) MS analysis, such as for example direct-spot MALDI-TOF or liquid chromatography MALDI-TOF mass spectrometry analysis. In some embodiments, the MS analysis comprises electrospray ionization (ESI) MS, such as for example liquid chromatography (LC) ESI-MS. Mass analysis can be accomplished using commercially-available spectrometers, such as for example triple quadrupole mass spectrometers. Methods for utilizing MS analysis, including MALDI-TOF MS and ESI-MS, to detect the presence and quantity of biomarker peptides in biological samples are known in the art. See for example U.S. Pat. Nos. 6,925,389; 6,989,100; and 6,890,763 for further guidance, each of which is incorporated by reference herein in its entirety. In some embodiments, the sample can be acidified with acetic acid, for example, to control sample pH and also ionization of weakly associated peptides off sample proteins prior to MS analysis.

The analysis of a plurality of markers can be carried out separately or simultaneously with one test sample. Several markers can be combined into one test for efficient processing of a multiple of samples. In addition, one skilled in the art would recognize the value of testing multiple samples (for example, at successive time points) from the same subject. Such testing of serial samples will allow the identification of changes in biomarker levels over time. Increases or decreases in marker levels, as well as the absence of change in marker levels, can provide useful information about the disease status that includes, but is not limited to identifying the approximate time from onset of the event, the appropriateness of various therapies, the effectiveness of various therapies, differentiation of the various types of CVD, identification of the disease severity, and identification of the subject's outcome, including risk of future events.

A panel consisting of biomarkers associated with a CVD (e.g., the biomarker peptides of Tables 2 and 3) can be constructed to provide relevant information related to the diagnosis or prognosis of the CVD and management of subjects with the CVD. Such a panel can be constructed, for example, using 1, 2, 3, 4, 5, 6, 7, 8, 9, 10, 15 or 20 individual biomarkers. The analysis of a single marker or subsets of markers comprising a larger panel of markers could be carried out by one skilled in the art to optimize clinical sensitivity or specificity in various clinical settings. These include, but are not limited to ambulatory, urgent care, critical care, intensive care, monitoring unit, insubject, outsubject, physician office, medical clinic, and health screening settings. Furthermore, one skilled in the art can use a single marker or a subset of markers comprising a larger panel of markers in combination with an adjustment of the diagnostic threshold in each of the aforementioned settings to optimize clinical sensitivity and specificity. The clinical sensitivity of an assay is defined as the percentage of those with the disease that the assay correctly predicts, and the specificity of an assay is defined as the percentage of those without the disease that the assay correctly predicts (34).

The analysis of markers could be carried out in a variety of physical formats as well. For example, the use of microtiter plates or automation could be used to facilitate the processing of large numbers of test samples. Alternatively, single sample formats could be developed to facilitate immediate treatment and diagnosis in a timely fashion, for example, in ambulatory transport or emergency room settings.

The presently disclosed subject matter further provides methods for treating a cardiovascular disease in a subject. In some embodiments, the methods comprise administering to a subject an effective amount of a fibrinopeptide A (FGA) polypeptide inhibitor molecule.

The term "effective amount" is used herein to refer to an amount of the therapeutic composition (e.g., a composition comprising an FGA antagonist) sufficient to produce a measurable biological response (e.g., a reduction in a biological activity of FGA). Actual dosage levels of active ingredients in a therapeutic composition of the presently disclosed subject matter can be varied so as to administer an amount of the active compound(s) that is effective to achieve the desired therapeutic response for a particular subject and/or application. The selected dosage level will depend upon a variety of factors including the activity of the therapeutic composition, formulation, the route of administration, combination with other drugs or treatments, severity of the condition being treated, and the physical condition and prior medical history of the subject being treated. Preferably, a minimal dose is administered, and dose is escalated in the absence of dose-limiting toxicity to a minimally effective amount. Determination and adjustment of a therapeutically effective dose, as well as evaluation of when and how to make such adjustments, are known to those of ordinary skill in the art of medicine.

The term "inhibitor" refers to a chemical substance that inactivates or decreases the biological activity of a polypeptide, such as FGA.

Suitable methods for administering to a subject a bioactive agent in accordance with the methods of the present subject matter include but are not limited to systemic administration, parenteral administration (including intravascular, intramuscular, intraarterial administration), intranasal delivery, oral delivery, buccal delivery, subcutaneous administration, inhalation, intratracheal installation, surgical implantation, transdermal delivery, local injection, and hyper-velocity injection/bombardment. Where applicable, continuous infusion can enhance drug accumulation at a target site (see, e.g., U.S. Pat. No. 6,180,082, incorporated herein by reference in its entirety).

The particular mode of administration used in accordance with the methods of the present subject matter depends on various factors, including but not limited to the bioactive agent and/or carrier employed, the severity of the condition to be treated, and mechanisms for metabolism or removal of the bioactive agent following administration.

For administration of a therapeutic composition as disclosed herein, conventional methods of extrapolating human dosage based on doses administered to a murine animal model can be carried out using the conversion factor for converting the mouse dosage to human dosage: Dose Human per kg=Dose Mouse per kg×12 (35). Drug doses can also be given in milligrams per square meter of body surface area because this method, rather than body weight, achieves a good correlation to certain metabolic and excretionary functions. Moreover, body surface area can be used as a common denominator for drug dosage in adults and children as well as in different animal species as described by Freireich et al. (35). Briefly, to express a mg/kg dose in any given species as the equivalent mg/sq m dose, multiply the dose by the appropriate km factor. In an adult human, 100 mg/kg is equivalent to 100 mg/kg×37 kg/sq m=3700 mg/m$^2$.

For oral administration, a satisfactory result can be obtained employing the FGA inhibitor in an amount ranging from about 0.01 mg/kg to about 100 mg/kg and preferably from about 0.1 mg/kg to about 30 mg/kg. A preferred oral dosage form, such as liquid suspensions, will contain the bioactive agent in an amount ranging from about 0.1 to about 500 mg, preferably from about 2 to about 50 mg, and more preferably from about 10 to about 25 mg.

For additional guidance regarding formulation and dose, see references (36-45), each of which is incorporated herein by reference.

The formulations administered to the subject can take such forms as aerosols, suspensions, solutions or emulsions in oily or aqueous vehicles, and can contain formulatory agents such as suspending, stabilizing and/or dispersing agents. Alternatively, the bioactive agent can be in powder form for constitution with a suitable vehicle, e.g., sterile pyrogen-free water, before use. Further, in some embodiments, the bioactive agent can be formulated for impregnation in clothing or barrier material, such as for example masks, gloves, surgical gowns, etc.

The formulations can be presented in unit-dose or multi-dose containers, for example sealed ampoules and vials, and can be stored in a frozen or freeze-dried (lyophilized) condition requiring only the addition of sterile liquid carrier immediately prior to use.

For oral administration, the compositions can take the form of, for example, tablets or capsules prepared by a conventional technique with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycollate); or wetting agents (e.g., sodium lauryl sulphate). The tablets can be coated by methods known in the art.

Liquid preparations for oral or intranasal administration can take the form of, for example, aerosols, solutions, syrups or suspensions, or they can be presented as a dry product for constitution with water or other suitable vehicle before use. Such liquid preparations can be prepared by conventional techniques with pharmaceutically acceptable additives such as suspending agents (e.g., sorbitol syrup, cellulose derivatives or hydrogenated edible fats); emulsifying agents (e.g. lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate. Preparations for oral administration can be suitably formulated to give controlled release of the active compound. For buccal administration the compositions can take the form of tablets or lozenges formulated in conventional manner.

The bioactive agents can also be formulated as a preparation for implantation or injection. Thus, for example, the bioactive agents can be formulated with suitable polymeric or hydrophobic materials (e.g., as an emulsion in an acceptable oil) or ion exchange resins, or as sparingly soluble derivatives (e.g., as a sparingly soluble salt).

The bioactive agents can also be formulated in rectal compositions (e.g., suppositories or retention enemas containing conventional suppository bases such as cocoa butter or other glycerides), creams or lotions, or transdermal patches.

Formulations described herein can further comprise a pharmaceutically acceptable carrier. Suitable formulations include aqueous and non-aqueous sterile injection solutions that can contain antioxidants, buffers, bacteriostats, bactericidal antibiotics and solutes that render the formulation isotonic with the bodily fluids of the intended recipient; and aqueous and non-aqueous sterile suspensions, which can include suspending agents and thickening agents. The pharmaceutically acceptable carriers or vehicles or excipients are well known to the one skilled in the art. For example, a pharmaceutically acceptable carrier or vehicle or excipient can be a 0.9% NaCl (e.g., saline) solution or a phosphate buffer. The pharmaceutically acceptable carrier or vehicle or excipients can be any compound or combination of compounds facilitating the administration of the bioactive agent; advantageously, the carrier, vehicle or excipient can facilitate administration, delivery and/or improve preservation of the bioactive agent and/or non-infectious virus.

Further with respect to the methods of the presently disclosed subject matter, a preferred subject is a vertebrate subject. A preferred vertebrate is warm-blooded; a preferred warm-blooded vertebrate is a mammal. A preferred mammal is most preferably a human. As used herein, the term "subject" includes both human and animal subjects. Thus, veterinary therapeutic uses are provided in accordance with the presently disclosed subject matter.

As such, the presently disclosed subject matter provides for the treatment and testing of mammals such as humans, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Also provided is the treatment of birds, including the treatment of those kinds of birds that are endangered and/or kept in zoos, as well as fowl, and more particularly domesticated fowl, i.e., poultry, such as turkeys, chickens, ducks, geese, guinea fowl, and the like, as they are also of economic importance to humans. Thus, also provided is the testing and treatment of livestock, including, but not limited to, domesticated swine, ruminants, ungulates, horses (including race horses), poultry, and the like.

In some embodiments, the subject tested and/or treated is afflicted with or was previously afflicted with a disease other than CVD. In particular, the other disease can be a disease linked to or predisposing one to CVD. For example, in some embodiments, the subject is a diabetic subject as diabetes can be a risk factor for developing CVD. Further, in some embodiments, the subject is suffering from an end stage renal disease, which may be chronic or acute, and may be secondary to a primary condition, including but not limited to diabetes, hypertension, lupus, nephrotic syndrome, polycystic kidney disease, interstitial nephritis, or cystinosis, It will be understood that various details of the presently disclosed subject matter can be changed without departing from the scope of the subject matter. Furthermore, the foregoing description is for the purpose of illustration only, and not for the purpose of limitation.

EXAMPLES

The following Examples have been included to illustrate modes of the presently disclosed subject matter. In light of the present disclosure and the general level of skill in the art, those of skill will appreciate that the following Examples are intended to be exemplary only and that numerous changes, modifications, and alterations can be employed without departing from the scope of the presently disclosed subject matter.

The following examples may include compilations of data that are representative of data gathered at various times during the course of development and experimentation related to the presently-disclosed subject matter.

Materials and Methods for Examples

Subject Characteristics.

Serum samples from 7 men without CAD and 11 men with CAD were evaluated. Seventy percent of the subjects were Caucasian. The two groups did not differ in age, hemoglobin, serum albumin, time on dialysis, or serum cholesterol (Table 1). The serum samples were obtained from storage in a biorepository at −80° C. All subjects had undergone cardiac catheterization during evaluation for kidney transplantation. Subjects were selected on the basis of the cardiac catheterization interpretation. CAD was defined as the presence of three vessel disease involvement and a description of severe CAD. The absence of CAD was defined as a normal catheterization study or minimal coronary artery disease. The serum samples were obtained within one month of cardiac catheterization. The study protocol was reviewed by the University of Louisville Human Studies Committee.

TABLE 1

|  | With CAD | Without CAD |
|---|---|---|
| Age (years) | 42 ± 11 | 51 ± 8 |
| Hemoglobin (g/dL) | 11.9 ± 1.3 | 11.6 ± 1.7 |
| Albumin (g/dL) | 3.7 ± 0.4 | 3.8 ± 0.5 |
| Cholesterol (mg/dL) | 184 ± 56 | 194 ± 67 |
| Dialysis Duration (Days) | 566 ± 207 | 566 ± 342 |

Figure 7:
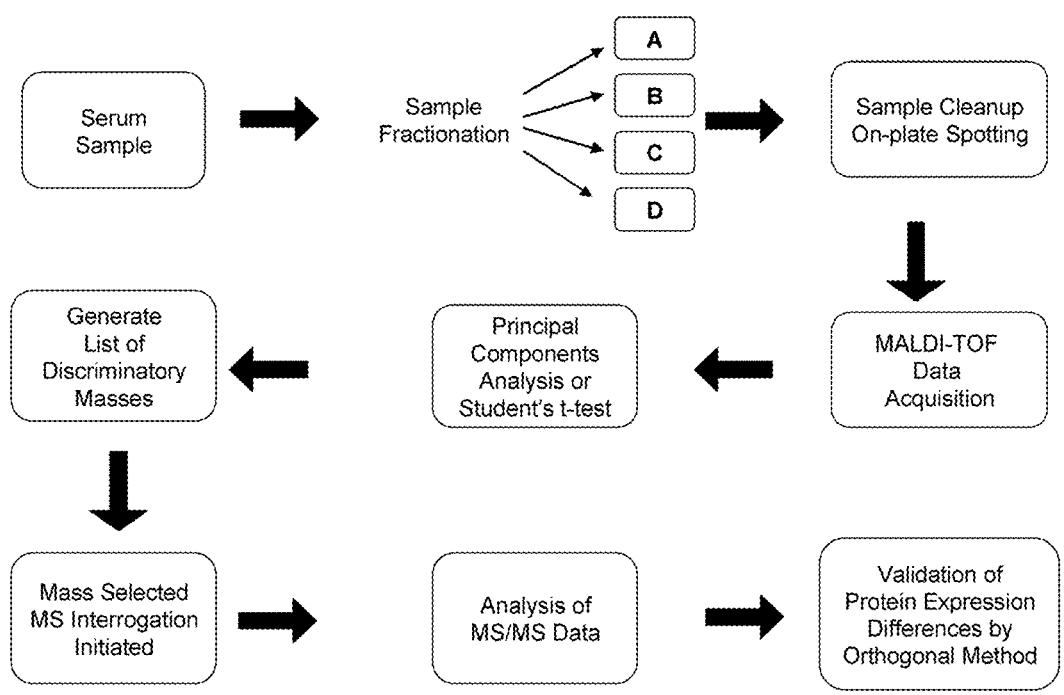
FIG. 7 is a flowchart showing candidate peptide biomarker discovery workflow. Serum samples were processed as described in the Methods section of the Examples to yield four panels of peptides including free whole serum peptides, free albumin/IgG depleted serum peptides, whole serum protein bound peptides, and albumin/IgG bound peptides. Peptide profiles for each of the four panels were compared using PCA and/or Student's t-test with the goal of generating a listed of differentially expressed peptide masses. Peptide sequence tags were generated using MALDI-TOF/TOF MS and Matrix Science Mascot assisted MS analysis.

Experimental Design:

An outline of the experimental workflow is provided in FIG. 7. The sample selection, handling and acquisition of peptide profiling data with MADLI-TOF MS were designed to minimize the introduction of bias in data analysis. All samples were assigned numbers randomly. Further randomization occurred with the order of sample preparation, sample lyophilization, MALDI-TOF plate spotting, and TOF and TOF/TOF data acquisition. Sample fractionation generated peptide panels consisting of free peptides, peptides that were bound to total serum proteins, peptides possibly released during the albumin/IgG immunodepletion, and peptides selectively bound to the highly abundant proteins, albumin and IgG. Analysis of differentially expressed peptides was conducted using PCA and Student's t-test, followed by manual review of ion intensities across all ion lists. Manual review was performed to ensure that peptides were not excluded due to incorrect base line normalization or baseline subtraction. Amino acid sequences construed from MALDI-TOF/TOF sequence tag analysis were validated using commercially synthesized peptides to recapitulate the MALDI-TOF/TOF analysis.

Sample Handling:

Samples were thawed once to aliquot into 100 μL volumes for further storage at −80° C. and once for sample preparation for peptide quantification. Samples were analyzed using two separate aliquots and individual aliquots were analyzed in triplicate. Serum samples were depleted of albumin and IgG using commercially available affinity spin columns (Sartorius N.A. Inc, Edgewood, N.Y.) according to the manufacturer's guidelines. Peptides not bound to serum proteins were isolated using a modification of the precipitation method of Chertov et al (31). Peptides bound to albumin and IgG were recovered from the albumin/IgG affinity resin by acid stripping with 10% acetic acid. Peptides bound to serum proteins were recovered from the organic solvent-coagulated proteins by salt or acid ionization. Recovered peptide solutions were lyophilized and resuspended in 0.1% trifluoroacetic acid (TFA) prior to MALDI-TOF MS analysis.

Analysis of Serum Peptides Using MALDI-TOF MS.

All samples were desalted and concentrated for MALDI-TOF MS analysis using C18 ZIPTIPS™ (Millipore, Billerica, Mass.). Peptides were eluted from the C18 resin using sample matrix, 5 mg/mL 4-hydroxy-α-cyanocinnamic acid (α-CN), and directly spotted onto the MALDI plate. Triplicate samples of each aliquot were spotted onto a MALDI-TOF target plate in positions chosen at random to prevent instrument or operator bias during data collection. Positive ion MALDI-TOF mass spectra were acquired using an Applied Biosystems Proteomics Analyzer (Model AB4700, Foster City, Calif.) operating in reflectron mode and with ion source pressure ~0.5 μTorr. After a 400 ns time-delayed ion extraction period, the ions were accelerated to 20 kV for TOF mass spectrometric analysis. A total of 1000 laser shots (355 nm Nd:YAG solid state laser operating at 200 Hz) were acquired and signal averaged. MALDI-TOF spectra were exported as .t2d files for comparison of peptide abundance by MARKERVIEW™ (Applied Biosystems). Peptides selected for further studies were analyzed using the AB4700 in TOF/TOF mode and interpretation of fragmentation data using MASCOT™ (Matrix Science, Boston, Mass.) ver1.9.

Analysis of MALDI-TOF MS Data Sets by MARKERVIEW™ Software.

Data files (.t2d) were exported from the AB4700 Proteomics Analyzer and imported into MARKERVIEW™ software. This software can find spectral peaks by user defined mass tolerance limits or bin spectra via user defined bin sizes. In addition, the user may define minimum and maximum signal responses, which assists in dealing with high-dimensional mass spectral data sets. Data were analyzed using data binning, which allowed for baseline subtraction. Following data import, the data were preprocessed using no-weighting and either mean-centered or Pareto data scaling prior to PCA. Peptides that sorted into groups were compared by Student's t-test to assess the statistical significance of the difference between the two groups. Differentially expressed peptides were selected for tandem MS analysis using the AB4700 Proteomics Analyzer.

Targeted LCMS Analysis of Selected Serum Peptides.

Aliquots (20 μL) of each sample from subjects with CAD were pooled and peptides isolated as described above. The process was repeated for samples from subjects without CAD. The isolated peptides were separated using nanoflow one-dimensional reversed phase chromatography and robotic fraction collection directly onto MALDI-TOF target plates. MADLI-TOF analysis.

Immunoblot Analysis.

Immunoblotting was performed as previously described (32, 33). Fifty micrograms of protein was subjected to 10% SDS-PAGE and immunoblot analysis with an anti-BMP-1 antibody (1:2000, B5058, Sigma-Aldrich, St. Louis, Mo.) raised against a peptide from the N-terminal domain of BMP-1 or anti-mTLD antibody (1:2000, AB81030, Chemicon International, Temecula, Calif.) raised against a peptide from the C-terminal domain of mTLD. Highly abundant proteins were immunosubtracted (ProteoPrep 20 Plasma Immunodepletion Kit, Sigma-Aldrich) from serum samples. Both high and low abundance serum protein fractions were used for immunoblot analysis of BMP-1 and mTLD expression.

Statistical Analysis of Data.

Principal component analysis of mass spectra was performed using MarkerView software. Differential peptide and protein expression was compared by an unpaired, two-tailed Student's t-test using aligned MALDI spectra and the peak cluster area for individual peptides. A p value of <0.05 was considered significant.

Results of Examples

Direct Analysis of Serum Peptide Abundance Using Matrix Assisted Laser Desorption Ionization (MALDI)—Time of Flight (TOF) Mass Spectrometry (MS)

The purpose of these experiments was to determine if serum peptides were differentially expressed in the serum of diabetic men with ESRD and CAD compared to diabetic men with ESRD and no CAD. To enrich analyte quantity and preserve any specific peptide interactions with intact proteins, serum samples were first fractionated to yield four peptide-containing fractions: unbound peptides present in whole serum; peptides bound to IgG and albumin; peptides released during depletion of IgG and albumin; and, peptides bound to proteins present after IgG and albumin depletion. Peptide expression data were first examined using principal component analysis (PCA). PCA is a method of exploratory data analysis that reduces the complexity of data, while retaining their variability, by transforming the data into a new group of variables, referred to as the principal components. PCA was used to obtain an unbiased assessment of whether or not the MALDI-TOF MS peptide expression data self-sorted into two groups corresponding to subjects with and without CAD. As shown in FIG. 1, the peptide expression data self sorted, suggesting differences in peptide expression between subjects with and without CAD.

Figure 2:
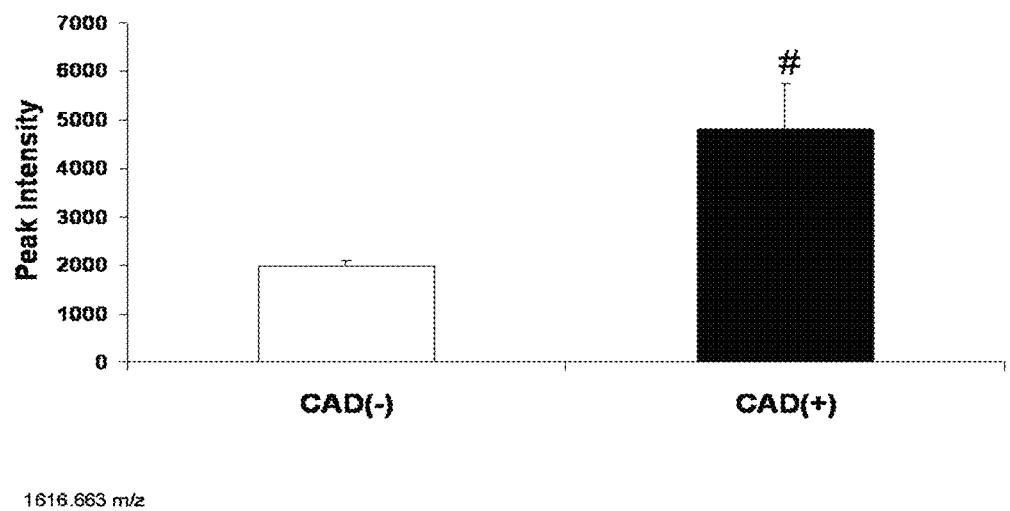
FIG. 2 is a graph showing average spectral intensities of a whole-serum-bound fragment of phosphorylated fibrinogen a chain (pFPA) (mass 1616.663 m/z; z=+1) in serum samples from subjects with and without CAD. Averaged spectral intensities (using total ion cluster area) demonstrate increased expression of the pFPA peptide fragment in serum of subjects with CAD (CAD(+), right bar) as compared to subjects without CAD (CAD(-), left bar) (#p<0.025). Data are presented as mean and standard error.
Figure 3:
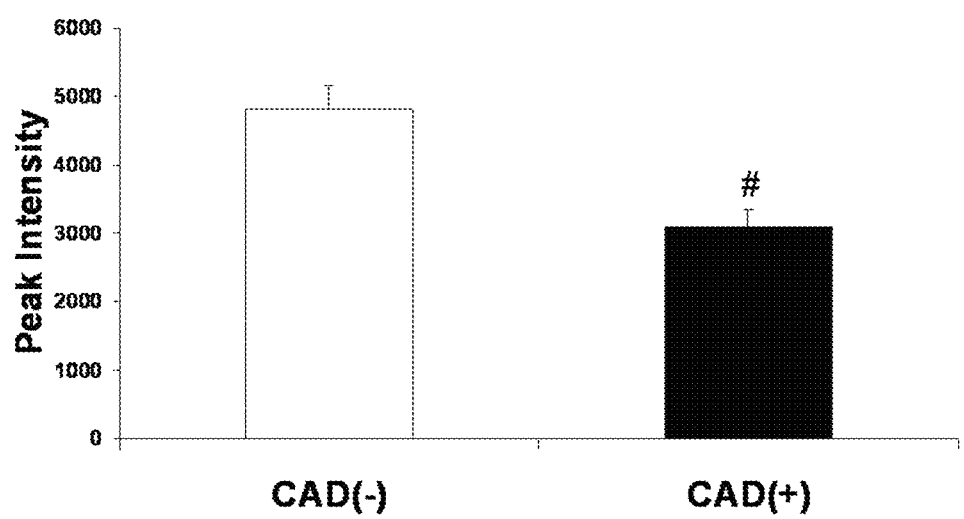
FIG. 3 is a graph showing average spectral intensities for a whole-serum-bound fragment of chondroitin beta-1,4-N-acetylgalactosaminyltransferase 2 (CSGalNAcT-2) (mass 1991.892 m/z; z=+1) in serum samples from subjects with and without CAD. Averaged spectral intensities (using total ion cluster area) demonstrate decreased expression of the CSGalNAcT-2 peptide fragment in the serum of subjects with CAD (CAD(+), right bar) as compared to subjects without CAD (CAD(-), left bar) (#p<0.001). Data are presented as mean and standard error.
Figure 4:
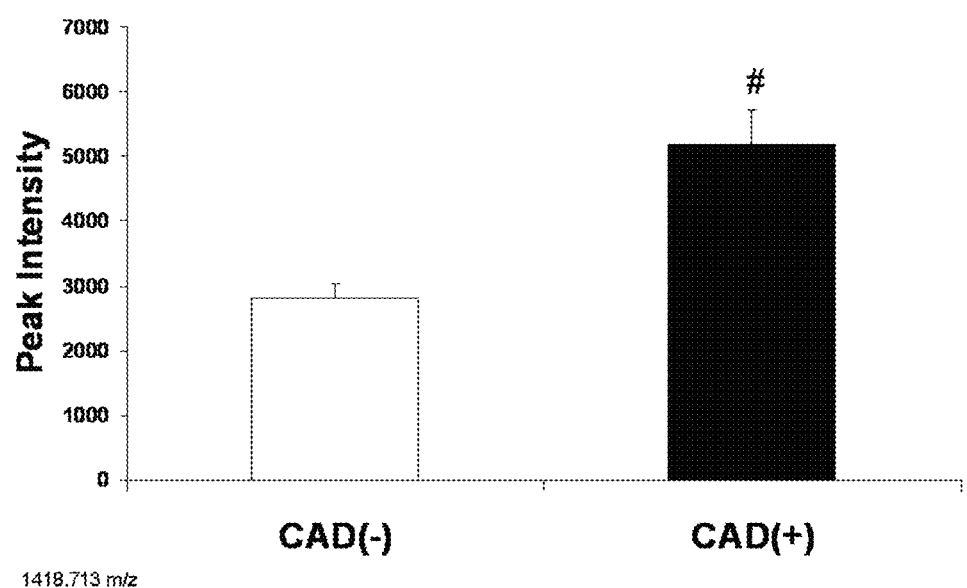
FIG. 4 is a graph showing average spectral intensities for a whole-serum-bound fragment of tolloid-like 2 protein (TLL-2) or bone morphogenetic protein-1 (BMP-1) (mass 1418.669 m/z; z=+1) in serum samples from subjects with and without CAD. Averaged spectral intensities (using total ion cluster area) demonstrate increased expression of the BMP-1/TLL-2 fragment in the serum of subjects with CAD (CAD(+), right bar) as compared to subjects without CAD (CAD(-), left bar (#p<0.025). Data are presented as mean and standard error.

To confirm this difference, the mass spectra from the subject samples was aligned and compared to the expression of each peptide between the two groups. Differences in expression of individual peptides were evaluated using Student's t-test. These analyses resulted in the identification of eight peptide masses whose expression was significantly different between the group of subjects with CAD and the group of subjects without CAD (Table 2 and FIGS. 2-4).

sequences returned by MASCOT sequence tag analysis. Four of the five peptides were successfully chemically synthesized and used to manually verify assignment of peptide fragmentation data and to confirm the original peptide amino acid sequence assignments.

TABLE 3

| Protein Name | Mass (m/z) | Accession No. | Gene Name | Proposed Amino Acid Sequence | Post-translational modification |
|---|---|---|---|---|---|
| Chondroitin beta-1,4-N-acetylgalactos-aminyltransferase 2 | 1991.896 | Q8N6G5 | CGAT2_HUMAN | Y.LLECAPQTDG NASLPGVVGE.N (SEQ ID NO: 6, SEQ ID NO: 12) | |
| Fibrinogen α-chain | 1616.663 | P02671 | FIBA_HUMAN | T.AD(pS)GEGDFLAE GGGVR.G (SEQ ID NO: 1, SEQ ID NO: 7) | Phosphorylation |
| Fibrinogen α-chain | 1465.675 | P02671 | FIBA_HUMAN | A.DSGEGDFLAE GGGVR.G (SEQ ID NO: 2, SEQ ID NO: 8) | |
| Tolloid-like 2 protein or Bone morphogenetic protein-1 | 1418.669 | Q9Y6L7 or P13497 | TLL-2_HUMAN or BMP1_HUMAN | H.FFSDKDECAK DN.G (SEQ ID NO: 3, SEQ ID NO: 9) | |
| Protocadherin-20 | 740.313 | Q8N6Y1 | PCD20_HUMAN | S.AGRPDPQ.S (SEQ ID NO: 5, SEQ ID NO: 11) | |

TABLE 2

| Peptide Sample Group | Observed Peptide Mass | Statistical Significance ($p<$) | Group with Increased Expression |
|---|---|---|---|
| Unbound Serum Peptides | 1896.015 | 0.025 | CAD |
| Whole-Serum-Bound Peptides | 740.313 | 0.01 | CAD |
| | 1140.584 | 0.05 | CAD |
| | 1418.669 | 0.001 | CAD |
| | 1465.665 | 0.025 | CAD |
| | 1545.545 | 0.01 | CAD |
| | 1616.663 | 0.025 | CAD |
| | 1991.892 | 0.001 | No CAD |

To ensure sufficient analyte for amino acid sequencing by tandem MS, two pools of serum were prepared, one containing an aliquot of serum from each subject in the group with CAD and the other containing an aliquot of serum from each subject in the group without CAD. Peptide sequence tagging by MALDI-TOF/TOF MS resulted in putative identifications for five peptide masses derived from four gene products (Table 3). These peptides were derived from a phosphorylated portion of the fibrinogen alpha chain 19-35 (pFPA): ($^{18}$T.AD(pS)GEGDFLAEGGGVR.G$^{36}$; SEQ ID NO: 1, SEQ ID NO: 7), a second sequence of the fibrinogen alpha chain 20-35 ($^{19}$A.DSGEGDFLAEGGGVR.G$^{36}$, SEQ ID NO: 2, SEQ ID NO: 8), tolloid-like 2 protein (TLL-2) 729-741 ($^{728}$H.FFSD-KDECAK DN.G$^{741}$; SEQ ID NO: 3, SEQ ID NO: 9) or bone morphogenetic protein-1 (BMP-1) 700-711 ($^{699}$H.FFSDK-DECSKDN.G$^{712}$; SEQ ID NO: 4, SEQ ID NO: 10), protocadherin-20 69-75 ($^{68}$S.AGRPDPQ.S$^{76}$; SEQ ID NO: 5, SEQ ID NO: 11) and chondroitin beta-1,4-N-acetylgalactosaminyltransferase 2 (CSGalNAcT-2) 31-50 ($^{30}$Y.LLECAPQTDG NASLPGVVGE.N$^{51}$; SEQ ID NO: 6, SEQ ID NO: 12). The sequence tag analysis could not discern between TLL-2 and BMP-1 as they are highly homologous and the peptide sequences of interest differed by a single amino acid (10). To validate the peptide identifications, the fragmentation data for the peptides was compared against fragmentation data for commercially synthesized peptides having the amino acid sequences returned by MASCOT sequence tag analysis. Four of the five peptides were successfully chemically synthesized and used to manually verify assignment of peptide fragmentation data and to confirm the original peptide amino acid sequence assignments.

Immunoblot Analysis of Mammalian Tolloid Protein (mTLD) and BMP-1

Figure 5:
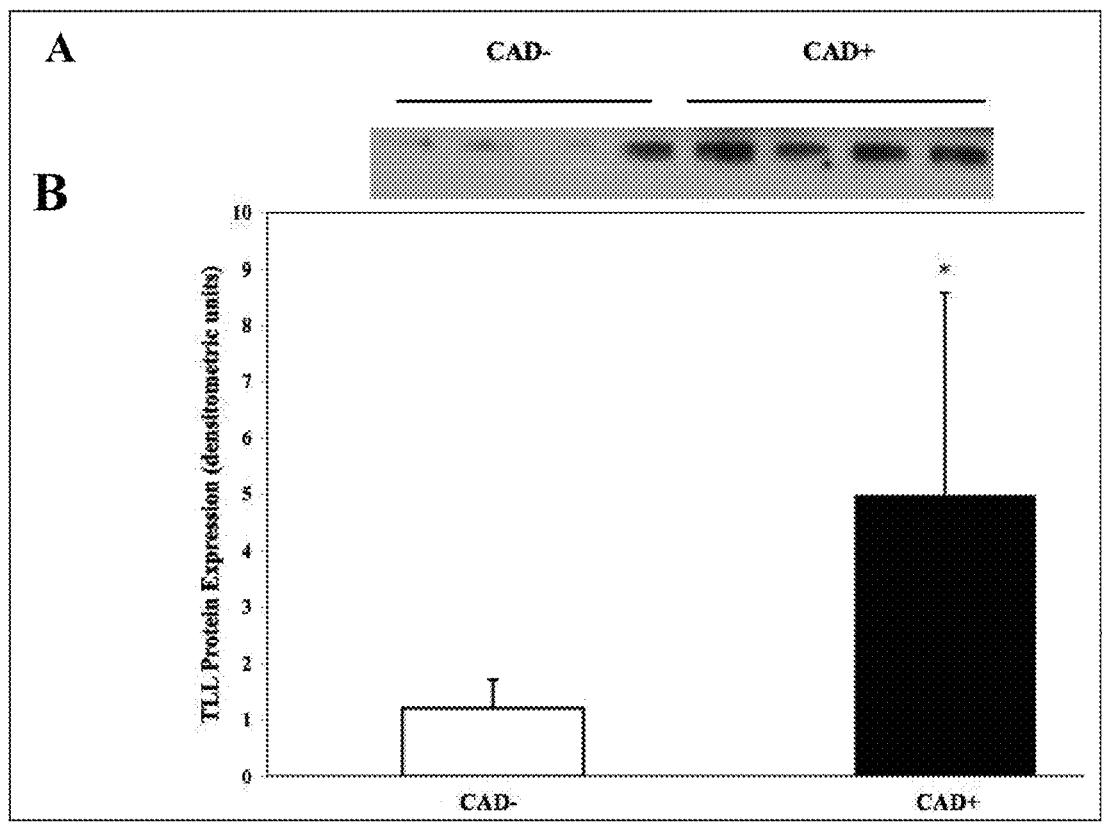
FIGS. 5A and 5B show intact mTLD bound to serum proteins is increased in serum from subjects with CAD. Serum samples from subjects with CAD (CAD+, n=8) and without CAD (CAD-, n=9) were specifically immunodepleted of the 20 most abundant proteins using a ProteoPrep20 spin column. These highly abundant proteins and co-immunodepleted proteins were eluted and analyzed by 1D-PAGE and immunoblotting for mTLD expression.
Figure 6:
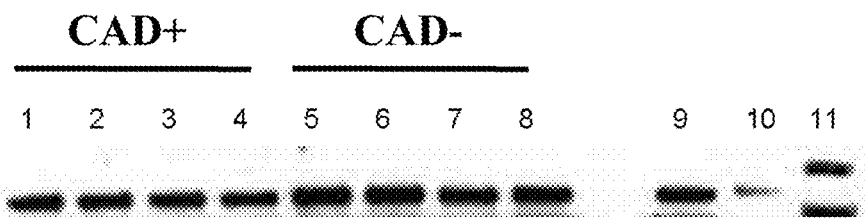
FIGS. 6A and 6B show intact (88 kDa) BMP-1 bound to highly abundant serum proteins is decreased in serum of subjects with CAD. Serum samples from subjects with CAD (CAD+, n=8) and without CAD (CAD-, n=9) were specifically immunodepleted of the 20 most abundant proteins using a ProteoPrep20 spin column. These highly abundant proteins and co-immunodepleted proteins were eluted and analyzed by 1D-PAGE and immunoblotting for BMP-1 expression.
Figure 6:
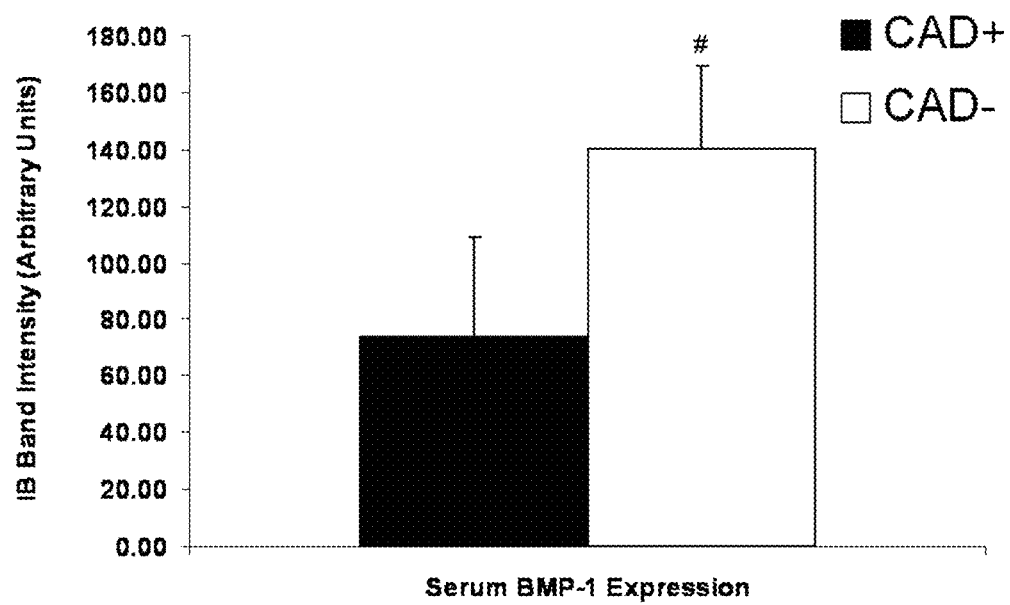

The presence of increased amounts of specific peptide fragments was then examined to determine if it might reflect changes in the amount of the corresponding intact protein. Immunoblots of mTLD and BMP-1 in whole serum were initially performed and no difference was found in expression between subjects with and without CAD. With the intent to decrease the dynamic range of protein concentrations, the samples were depleted of the twenty most abundant proteins using a commercial affinity column (Proteoprep 20 Plasma Immunodepletion Kit, Sigma-Aldrich). Immunoblot for mTLD and BMP-1 of the low abundance serum fraction again showed no difference between the groups. Because BMP-1 can bind to abundant plasma proteins such as alpha-2 macroglobulin, (11) the fraction removed by the immunoaffinity column for both mTLD and BMP-1 was then immunoblotted. Protein bound mTLD was significantly increased in serum from subjects with CAD compared to subjects without CAD (FIG. 5), while protein-bound BMP-1 expression was significantly decreased (FIG. 6).

Discussion of the Examples

Cardiovascular diseases are the major cause of mortality in the general population, but even more so in subpopulations with significant underlying health issues, including in particular subjects with chronic kidney disease. The failure of traditional risk factors for the general population to fully explain the risk of CVDs in subpopulations has led to a search for alternative, or non-traditional, risk factors.

A large number of individual biomarkers of coronary heart disease in the general population have been proposed, including C-reactive protein (CRP), (12) homocysteine, (13, 14) fibrinogen, (15) and fibrin fragment D-dimer (16). To date, incorporation of these non-traditional risk factors into the algorithms used to assess risk of CVDs such as CAD has not markedly improved risk prediction in the general population, as demonstrated by Wang and colleagues who found only a small increase in the ability to classify risk when 10 biomarkers were used in a multivariate analysis adjusted for the conventional risk factors (17). Risk prediction for CVDs in hemodialysis subjects is even more fraught with difficulty. Both traditional and new risk assessment tools may not predict CVDs in hemodialysis subjects. Recently, Weiner et al reported that the Framingham Risk Assessment Instrument performed poorly in predicting cardiovascular events in subjects with chronic kidney disease (18). Furthermore, some specific biomarkers that are thought to predict disease in the general population may not be as predictive in hemodialysis subjects. For example, C-reactive protein and interleukin-6 may not be good surrogates for all inflammatory cardiovascular risk factors in hemodialysis subjects (19). Finally, chronic kidney disease itself may be an independent risk factor for cardiovascular diseases (20). Clearly, improved methods to assess CVDs in the general population and subpopulations (e.g., renal subjects) are needed.

One objective of the present examples was to determine if there are peptides in biological samples that can discriminate between subjects having no significant CVD and those with significant CAD. In these examples, subjects were limited to diabetic subjects with ESRD having no significant CAD and those with significant CAD to control for variables between subjects and because this subpopulation suffers disproportionately from CVDs. It was further reasoned that, if such discriminating peptides could be identified, they could provide new insights into the pathophysiology of CVDs, and CAD in particular, in ESRD and in diabetes. The present examples identified 8 peptides that are differentially expressed in the serum of individuals that have developed CAD as compared to well-matched controls. Of the eight peptides, the protein from which these peptides were derived was identified in five instances.

The peptides were isolated from four serum fractions before MS analysis as outlined in the Methods and Results of the present examples. The peptide fractions isolated were unbound peptides present in whole serum, peptides bound to the IgG and albumin fraction, peptides released during depletion of IgG and albumin, and peptides bound to proteins present after IgG and albumin depletion. The rationale for this approach was based in part that the dynamic range of protein concentrations in serum is greater than $10^{12}$, a range that exceeds the dynamic range of detection by MS. Isolation of peptides into sub-groups can decrease the dynamic range of expression and enrich analytes for characterization.

The eight candidate peptide biomarkers were identified using a peptidomic approach. Peptidomics can be defined as the quantitative and qualitative study of peptides expressed within a given biological system in a time dependent fashion. Peptidomic studies typically use a top-down mass spectrometric analysis in that no enzymatic or proteolytic alterations are needed prior to MS interrogation. Recently, high-resolution, top-down MS methods, as employed in the present study, have been successfully applied to the diagnosis of disease. These analytical tools, which include capillary electrophoresis (CE), electrospray ionization (ESI), and LC-MALDI-TOF MS, have been used to isolate endogenous peptides from serum, plasma and urine that predict clinical outcomes in congenital disorders or are diagnostic of malignancy (25-27). The same approaches have been applied to the discovery of biomarker candidates of CAD (28). Recently, Zimmerli et al used CE coupled to ESI-MS to identify urinary polypeptides predictive of CAD (29). The majority of the candidate CAD peptide biomarkers identified by Zimmerli et al were derived from collagen. Donahue et al used LC coupled to ESI-MS to analyze the low molecular weight protein fraction (less than 20 kDa) present in plasma from subjects with and without CAD (30). Individual plasma samples were pooled in their study to enrich the low molecular weight fraction. They observed differential expression of 95 peptides between the two groups. There is little overlap between the findings herein and those of Donahue et al. This lack of agreement may be a result of the differences between the two studies in sample handling, pooling of samples, or the mass spectrometry approach used.

The present examples examined whether serum peptide fragments reflect changes in intact proteins. These peptide data had indicated increased expression of a fragment of either TLL-2 or BMP-1 in serum from subjects with CAD. Because BMP-1, mTLD, TLL-1 and TLL-2 are very homologous, additional immunoblots were first performed with an antibody that recognizes mTLD, TLL-1 and TLL-2, but not BMP-1. These studies showed increased expression of mTLD, but not TLL-1 and TLL-2 in serum from subjects with CAD (FIG. 5). Immunoblots of serum were then performed using an antibody that recognizes the N-terminal peptide region in BMP-1. The 88 kDa band migrating with the BMP-1 positive control was increased in serum from subjects without CAD (FIG. 6). Furthermore, only protein bound BMP-1 and mTLD were significantly different between clinical groups. No difference in unbound BMP-1 or mTLD expression was seen between subjects with and without CAD.

In summary, the present examples provide data identifying a series of biomarkers for CVD in biological samples from a cohort of well-characterized subjects. The presently-disclosed data demonstrate that proteins from which these peptides are derived exhibit changes that may reflect alterations of intact serum protein concentrations. Thus, these peptides can serve as biomarkers for CVDs.

REFERENCES

1. Ohtake T, Kobayashi S, Moriya H, et al.: High prevalence of occult coronary artery stenosis in subjects with chronic kidney disease at the initiation of renal replacement therapy: an angiographic examination. *J Am Soc Nephrol* 16:1141-1148, 2005
2. Hase H, Joki N, Ishikawa H, et al.: Independent risk factors for progression of coronary atherosclerosis in hemodialysis subjects. *Ther Apher Dial* 10:321-327, 2006
3. Hase H, Tsunoda T, Tanaka Y, et al.: Risk factors for de novo acute cardiac events in subjects initiating hemodialysis with no previous cardiac symptom. *Kidney Int* 70:1142-1148, 2006
4. Parekh R S, Zhang L, Fivush B A, et al.: Incidence of atherosclerosis by race in the dialysis morbidity and mortality study: a sample of the US ESRD population. *J Am Soc Nephrol* 16:1420-1426, 2005
5. Trespalacios F C, Taylor A J, Agodoa L Y, et al.: Incident acute coronary syndromes in chronic dialysis subjects in the United States. *Kidney Int* 62:1799-1805, 2002
6. Herzog C A, Ma J Z, Collins A J: Poor long-term survival after acute myocardial infarction among subjects on long-term dialysis. *N Engl J Med* 339:799-805, 1998
7. Charytan D, Mauri L, Agarwal A, et al.: The use of invasive cardiac procedures after acute myocardial infarction in long-term dialysis subjects. *Am Heart J* 152:558-564, 2006
8. Zager P G, Nikolic J, Brown R H, et al.: "U" curve association of blood pressure and mortality in hemodialysis subjects. Medical Directors of Dialysis Clinic, Inc. *Kidney Int* 54:561-569, 1998
9. Liu Y, Coresh J, Eustace J A, et al.: Association between cholesterol level and mortality in dialysis subjects: role of inflammation and malnutrition. *Jama* 291:451-459, 2004
10. Scott I C, Blitz I L, Pappano W N, et al.: Mammalian BMP-1/Tolloid-related metalloproteinases, including novel family member mammalian Tolloid-like 2, have differential enzymatic activities and distributions of expression relevant to patterning and skeletogenesis. *Dev Biol* 213:283-300, 1999

11. Zhang Y, Ge G, Greenspan D S: Inhibition of bone morphogenetic protein 1 by native and altered forms of alpha2-macroglobulin. *J Biol Chem* 281:39096-39104, 2006

12. Cushman M, Arnold A M, Psaty B M, et al.: C-reactive protein and the 10-year incidence of coronary heart disease in older men and women: the cardiovascular health study. *Circulation* 112:25-31, 2005

13. Mangoni A A, Jackson S H: Homocysteine and cardiovascular disease: current evidence and future prospects. *Am J Med* 112:556-565, 2002

14. Danesh J, Lewington S, Thompson S G, et al.: Plasma fibrinogen level and the risk of major cardiovascular diseases and nonvascular mortality: an individual participant meta-analysis. *Jama* 294:1799-1809, 2005

15. Danesh J, Collins R, Appleby P, et al.: Association of fibrinogen, C-reactive protein, albumin, or leukocyte count with coronary heart disease: meta-analyses of prospective studies. *Jama* 279:1477-1482, 1998

16. Danesh J, Whincup P, Walker M, et al.: Fibrin D-dimer and coronary heart disease: prospective study and meta-analysis. *Circulation* 103:2323-2327, 2001

17. Wang T J, Gona P, Larson M G, et al.: Multiple biomarkers for the prediction of first major cardiovascular events and death. *N Engl J Med* 355:2631-2639, 2006

18. Weiner D E, Tighiouart H, Elsayed E F, et al.: The Framingham predictive instrument in chronic kidney disease. *J Am Coll Cardiol* 50:217-224, 2007

19. Kaysen G A, Levin N W, Mitch W E, et al.: Evidence that C-reactive protein or IL-6 are not surrogates for all inflammatory cardiovascular risk factors in hemodialysis subjects. *Blood Purif* 24:508-516, 2006

20. Go A S, Chertow G M, Fan D, et al.: Chronic kidney disease and the risks of death, cardiovascular events, and hospitalization. *N Engl J Med* 351:1296-1305, 2004

21. Lopez M F, Mikulskis A, Kuzdzal S, et al.: A novel, high-throughput workflow for discovery and identification of serum carrier protein-bound peptide biomarker candidates in ovarian cancer samples. *Clin Chem* 53:1067-1074, 2007

22. Kuzdzal S, Lopez M, Mikulskis A, et al.: Biomarker discovery and analysis platform: application to Alzheimer's disease. *Biotechniques* 39:606-607, 2005

23. Petricoin E F, Belluco C, Araujo R P, et al.: The blood peptidome: a higher dimension of information content for cancer biomarker discovery. *Nat Rev Cancer* 6:961-967, 2006

24. Lowenthal M S, Mehta A I, Frogale K, et al.: Analysis of albumin-associated peptides and proteins from ovarian cancer subjects. *Clin Chem* 51:1933-1945, 2005

25. Villanueva J, Martorella A J, Lawlor K, et al.: Serum peptidome patterns that distinguish metastatic thyroid carcinoma from cancer-free controls are unbiased by gender and age. *Mol Cell Proteomics* 5:1840-1852, 2006

26. Villanueva J, Philip J, Chaparro C A, et al.: Correcting common errors in identifying cancer-specific serum peptide signatures. *J Proteome. Res.* 4:1060-1072, 2005

27. Decramer S, Wittke S, Mischak H, et al.: Predicting the clinical outcome of congenital unilateral ureteropelvic junction obstruction in newborn by urinary proteome analysis. *Nat Med* 12:398-400, 2006

28. Martin-Ventura J L, Blanco-Colio L M, Tunon J, et al.: Proteomics in atherothrombosis: a future perspective. *Expert Rev Proteomics* 4:249-260, 2007

29. Zimmerli L U, Schiffer E, Zurbig P, et al.: Urinary proteomic biomarkers in coronary artery disease. *Mol Cell Proteomics,* 2007

30. Donahue M P, Rose K, Hochstrasser D, et al.: Discovery of proteins related to coronary artery disease using industrial-scale proteomics analysis of pooled plasma. *Am Heart J* 152:478-485, 2006

31. Chertov O, Biragyn A, Kwak L W, et al.: Organic solvent extraction of proteins and peptides from serum as an effective sample preparation for detection and identification of biomarkers by mass spectrometry. *Proteomics* 4:1195-1203, 2004

32. Rane M J, Pan Y, Singh S, et al.: Heat shock protein 27 controls apoptosis by regulating Akt activation. *J Biol. Chem.* 278:27828-27835, 2003

33. Rane M J, Gozal D, Butt W, et al.: Gamma-amino butyric acid type B receptors stimulate neutrophil chemotaxis during ischemia-reperfusion. *J Immunol.* 174:7242-7249, 2005

34. Tietz Textbook of Clinical Chemistry, 2nd edition, Carl Burtis and Edward Ashwood eds., W.B. Saunders and Company, p. 496

35. Freireich et al., (1966) *Cancer Chemother Rep.* 50:219-244

36. U.S. Pat. No. 5,326,902

37. U.S. Pat. No. 5,234,933

38. PCT International Publication No. WO 93/25521

39. Berkow et al., (1997) The Merck Manual of Medical Information, Home ed. Merck Research Laboratories, Whitehouse Station, N.J.

40. Goodman et al., (1996) Goodman & Gilman's the Pharmacological Basis of Therapeutics, 9th ed. McGraw-Hill Health Professions Division, New York 41. Ebadi, (1998) CRC Desk Reference of Clinical Pharmacology. CRC Press, Boca Raton, Fla.

42. Katzung, (2001) Basic & Clinical Pharmacology, 8th ed. Lange Medical Books/McGraw-Hill Medical Pub. Division, New York 43. Remington et al., (1975) Remington's Pharmaceutical Sciences, 15th ed. Mack Pub. Co., Easton, Pa.

44. Speight et al., (1997) Avery's Drug Treatment: A Guide to the Properties, Choice, Therapeutic Use and Economic Value of Drugs in Disease Management, 4th ed. Adis International, Auckland/Philadelphia 45. Duch et al., (1998) *Toxicol. Lett.* 100-101:255-263

It will be understood that various details of the presently disclosed subject matter can be changed without departing from the scope of the presently disclosed subject matter. Furthermore, the foregoing description is for the purpose of illustration only, and not for the purpose of limitation.

What is claimed is:

1. A method for diagnosing a cardiovascular disease in a subject, comprising:
   (a) determining an amount of at least one peptide in a biological sample from the subject, the at least one peptide having an amino acid sequence comprising sequence identification number 7 (SEQ ID NO:7), and
   (b) comparing the amount of the at least one peptide in the sample with a control level, wherein if the amount determined in (a) is different than the control level, the subject is diagnosed as having, or at an increased risk of developing, the cardiovascular disease.

2. The method of claim 1, wherein determining the amount of the at least one peptide comprises determining the amount of the at least one peptide in the sample using mass spectrometry (MS) analysis, immunoassay analysis, or both.

3. The method of claim 2, wherein the MS analysis comprises matrix-assisted laser desorption/ionization (MALDI) time-of-flight (TOF) MS analysis or electrospray ionization (ESI) MS.

4. The method of claim 3, wherein the MALDI-TOF MS analysis is direct-spot MALDI-TOF or liquid chromatography MALDI-TOF mass spectrometry analysis.

5. The method of claim 2, wherein the immunoassay analysis comprises an enzyme-linked immunosorbent assay (ELISA).

6. The method of claim 1, wherein the at least one peptide is isolated from a fraction of the sample selected from the group consisting of a bound fraction and an unbound fraction.

7. The method of claim 6, wherein the hound fraction is a fraction selected from the group consisting of an albumin-bound fraction and an immunoglobulin-bound fraction.

8. The method of claim 1, wherein the at least one peptide is a plurality of peptides.

9. The method of claim 1, wherein the sample is selected from the group consisting of a saliva sample, a blood sample, a serum sample, a plasma sample, and a urine sample.

10. The method of claim 1, wherein the subject is human.

11. The method of claim 1, wherein the subject is a diabetic subject.

12. The method of claim 1, wherein the cardiovascular disease is a coronary artery disease (CAD), a peripheral vascular disease, or both.

13. The method of claim 12, wherein the CAD comprises atherosclerosis.

14. A method for determining treatment efficacy and/or progression of a cardiovascular disease in a subject, comprising:
(a) determining an amount of at least one peptide in a first biological sample collected from the subject at a first time point, the at least one peptide having an amino acid sequence comprising sequence identification number 7 (SEQ ID NO:7),
(b) determining an amount of the at least one peptide comprising sequence identification number 7 (SEQ ID NO:7), in a second biological sample from the subject at a second time point; and
(c) comparing the amounts of the at least one peptide in the first and second samples, wherein a change in the amounts of the at least one peptide from the first and second samples is correlated with determining treatment efficacy and/or progression of the cardiovascular disease in the subject.

15. The method of claim 14, wherein determining the amount of the at least one peptide in the first and second biological samples comprises quantitating the amount of the at least one peptide in the samples using mass spectrometry (MS) analysis, immunoassay analysis, or both.

16. The method of claim 15, wherein the MS analysis comprises matrix-assisted laser desorption/ionization (MALDI) time-of-flight (TOF) MS analysis or electrospray ionization (ESI) MS.

17. The method of claim 16, wherein the MALDI-TOF MS analysis is direct-spot MALDI-TOF or liquid chromatography MALDI-TOF mass spectrometry analysis.

18. The method of claim 15, wherein the immunoassay analysis comprises an enzyme-linked immunosorbent assay (ELISA).

19. The method of claim 14, wherein the at least one peptide is isolated from a fraction of the sample selected from the group consisting of a bound fraction and an unbound fraction.

20. The method of claim 19, wherein the bound fraction is a fraction selected from the group consisting of an albumin-bound fraction and an immunoglobulin-bound fraction.

21. The method of claim 14, wherein the at least one peptide is a plurality of peptides.

22. The method of claim 14, wherein in the first and second biological samples are independently selected from the group consisting of a saliva sample, a blood sample, a serum sample, a plasma sample, and a urine sample.

23. The method of claim 14, wherein the subject is human.

24. The method of claim 14, wherein the subject is a diabetic subject.

25. The method of claim 14, wherein the cardiovascular disease is a coronary artery disease (CAD), a peripheral vascular disease, or both.

26. The method of claim 25, wherein the CAD comprises atherosclerosis.

27. The method of claim 14, wherein the first time point is prior to initiation of a treatment for the cardiovascular disease and the second time point is after initiation of the treatment.

28. The method of claim 14, wherein the first time point is prior to onset of the cardiovascular disease and the second time point is after onset of the cardiovascular disease.

* * * * *

UNITED STATES PATENT AND TRADEMARK OFFICE
CERTIFICATE OF CORRECTION

PATENT NO. : 8,703,435 B2  Page 1 of 1
APPLICATION NO. : 12/596814
DATED : April 22, 2014
INVENTOR(S) : Klein et al.

It is certified that error appears in the above-identified patent and that said Letters Patent is hereby corrected as shown below:

IN THE CLAIMS:

In Claim 1, line 64 of Column 27, "(SEQ ID NO:7), and" should read --(SEQ ID NO: 7); and--.

In Claim 7, line 10 of Column 29, "hound" should read --bound--.

In Claim 14, line 33 of Column 29, "(SEQ ID NO:7)," should read --(SEQ ID NO: 7);--.
In Claim 14, line 36 of Column 29, "NO:7), in" should read --NO: 7) in--.

Signed and Sealed this
Twenty-ninth Day of July, 2014

Michelle K. Lee
*Deputy Director of the United States Patent and Trademark Office*

SEQUENCE LISTING

<160> NUMBER OF SEQ ID NOS: 12

<210> SEQ ID NO 1
<211> LENGTH: 18
<212> TYPE: PRT
<213> ORGANISM: Homo sapiens

<400> SEQUENCE: 1

Thr Ala Asp Ser Gly Glu Gly Asp Phe Leu Ala Glu Gly Gly Gly Val
1               5                   10                  15

Arg Gly

<210> SEQ ID NO 2
<211> LENGTH: 17
<212> TYPE: PRT
<213> ORGANISM: Homo sapiens

<400> SEQUENCE: 2

Ala Asp Ser Gly Glu Gly Asp Phe Leu Ala Glu Gly Gly Gly Val Arg
1               5                   10                  15

Gly

<210> SEQ ID NO 3
<211> LENGTH: 14
<212> TYPE: PRT
<213> ORGANISM: Homo sapiens

<400> SEQUENCE: 3

His Phe Phe Ser Asp Lys Asp Glu Cys Ala Lys Asp Asn Gly
1               5                   10

<210> SEQ ID NO 4
<211> LENGTH: 14
<212> TYPE: PRT
<213> ORGANISM: Homo sapiens

<400> SEQUENCE: 4

His Phe Phe Ser Asp Lys Asp Glu Cys Ser Lys Asp Asn Gly
1               5                   10

<210> SEQ ID NO 5
<211> LENGTH: 9
<212> TYPE: PRT
<213> ORGANISM: Homo sapiens

<400> SEQUENCE: 5

Ser Ala Gly Arg Pro Asp Pro Gln Ser
1               5

<210> SEQ ID NO 6
<211> LENGTH: 22
<212> TYPE: PRT
<213> ORGANISM: Homo sapiens

<400> SEQUENCE: 6

Tyr Leu Leu Glu Cys Ala Pro Gln Thr Asp Gly Asn Ala Ser Leu Pro
1               5                   10                  15

Gly Val Val Gly Glu Asn
                20

<210> SEQ ID NO 7
<211> LENGTH: 16

```
<212> TYPE: PRT
<213> ORGANISM: Homo sapiens

<400> SEQUENCE: 7

Ala Asp Ser Gly Glu Gly Asp Phe Leu Ala Glu Gly Gly Val Arg
1               5                   10                  15

<210> SEQ ID NO 8
<211> LENGTH: 14
<212> TYPE: PRT
<213> ORGANISM: Homo sapiens

<400> SEQUENCE: 8

Asp Ser Gly Glu Gly Asp Phe Leu Ala Glu Gly Gly Val Arg
1               5                   10

<210> SEQ ID NO 9
<211> LENGTH: 12
<212> TYPE: PRT
<213> ORGANISM: Homo sapiens

<400> SEQUENCE: 9

Phe Phe Ser Asp Lys Asp Glu Cys Ala Lys Asp Asn
1               5                   10

<210> SEQ ID NO 10
<211> LENGTH: 12
<212> TYPE: PRT
<213> ORGANISM: Homo sapiens

<400> SEQUENCE: 10

Phe Phe Ser Asp Lys Asp Glu Cys Ser Lys Asp Asn
1               5                   10

<210> SEQ ID NO 11
<211> LENGTH: 7
<212> TYPE: PRT
<213> ORGANISM: Homo sapiens

<400> SEQUENCE: 11

Ala Gly Arg Pro Asp Pro Gln
1               5

<210> SEQ ID NO 12
<211> LENGTH: 20
<212> TYPE: PRT
<213> ORGANISM: Homo sapiens

<400> SEQUENCE: 12

Leu Leu Glu Cys Ala Pro Gln Thr Asp Gly Asn Ala Ser Leu Pro Gly
1               5                   10                  15

Val Val Gly Glu
            20
```